(12) United States Patent
Abdel-Aziz et al.

(10) Patent No.: US 12,139,461 B1
(45) Date of Patent: Nov. 12, 2024

(54) PIPERIDINE COMPOUNDS AS PDE5 INHIBITORS

(71) Applicant: KING SAUD UNIVERSITY, Riyadh (SA)

(72) Inventors: Alaa Abdel-Moenes Abdel-Aziz, Riyadh (SA); Adel Shaaban Azab Morsy, Riyadh (SA); Sabry Mohamed Abdo Attia, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/642,707

(22) Filed: Apr. 22, 2024

(51) Int. Cl.
| | | |
|---|---|---|
| *C07D 211/96* | (2006.01) | |
| *A61K 31/451* | (2006.01) | |
| *A61P 15/10* | (2006.01) | |
| *C07D 211/14* | (2006.01) | |
| *C12N 9/99* | (2006.01) | |

(52) U.S. Cl.
CPC .......... *C07D 211/96* (2013.01); *A61K 31/451* (2013.01); *A61P 15/10* (2018.01); *C07D 211/14* (2013.01); *C12N 9/99* (2013.01)

(58) Field of Classification Search
CPC ...... C07D 211/96; C07D 211/14; C12N 9/99; A61P 15/10; A61K 31/451
See application file for complete search history.

(56) References Cited

U.S. PATENT DOCUMENTS

| | | |
|---|---|---|
| 2002/0151552 A1 | 10/2002 | Badwan |
| 2005/0043364 A1 | 2/2005 | Kennedy |

OTHER PUBLICATIONS

Xiong et al., 226 Euro. J. Med. Chem. 113879 (2021) (Year: 2021).*
Dawood et al.; "Synthesis, identification and molecular docking studies of N-functionalized piperidine derivatives linked to 1,2,3-triazole ring"; Synthetic Communications, an International Journal for Rapid Communication of Synthetic Organic Chemistry; Rafid S. Dawood & Sudad A. Dayl (2020): Synthetic Communications, DOI: 10.1080/00397911.2020.1776876 to link to this article: https://doi.org/10.1080/00397911.2020.1776876.
Swami Prabhuling et al.; "Synthesis and Modeling Studies of Furoxan Coupled Spiro-Isoquinolino Piperidine Derivatives as No Releasing PDE 5 Inhibitors"; Biomedicines. May 2020; 8(5): 121. Published online May 14, 2020. doi: 10.3390/biomedicines8050121 PMCID: PMC7277557 PMID: 32423159.
Ahmed K. ElHady et al.; "Advancements in Phosphodiesterase 5 Inhibitors: Unveiling Present and Future Perspectives"; Pharmaceuticals 2023, 16(9), 1266; https://doi.org/10.3390/ph16091266 / Revised: Aug. 25, 2023 / Accepted: Sep. 5, 2023 / Published: Sep. 6, 2023 (This article belongs to the Special Issue Feature Reviews in Medicinal Chemistry).
Yevgeniya Antonova-Koch et al.; "Open-source discovery of chemical leads for next-generation chemoprotective antimalarials"; Science. 2018; 362(6419): eaat9446. Published online Dec. 7, 2018. doi: 10.1126/science.aat9446 PMCID: PMC6516198, NIHMSID: NIHMS1029139 PMID: 30523084.

* cited by examiner

*Primary Examiner* — Timothy R Rozof
(74) *Attorney, Agent, or Firm* — Nath, Goldberg & Meyer; Joshua B. Goldberg

(57) ABSTRACT

Novel 1,4-disubstituted piperidine derivatives, a method of synthesizing said compounds, a pharmaceutical composition comprising said compounds and a suitable carrier, and a method of using the compounds. The 1,4-disubstituted piperidine derivatives compounds, identified as PDE5 inhibitors, are useful for the treatment of erectile dysfunction.

3 Claims, 4 Drawing Sheets

PIPERIDINE COMPOUNDS AS PDE5 INHIBITORS

BACKGROUND

1. Field

The present disclosure provides novel 1,4-disubstituted piperidine derivatives that inhibit PDE5 activity, compositions containing such compounds, and methods of their preparation. These compounds and compositions are useful as therapeutic agents for erectile dysfunction.

2. Description of the Related Art

Phosphodiesterase type 5 (PDE5) is an enzyme that catalyzes the hydrolysis of the cyclic nucleotide cGMP into guanosine monophosphates, therefore regulating cGMP-specific signaling pathways. It plays an essential role in regulating physiological processes like relaxation and contraction of smooth muscle. The major PDE isozyme found in the tissue of the penile corpus cavernosum is crucial in the regulation of penile erection.

Erectile dysfunction (ED) is a widespread medical condition that affects millions of men and their sexual partners throughout the world. ED is the inability to obtain or maintain an erection strong enough for satisfactory sexual performance. Most individuals' mechanistic basis for ED is complicated and multivariate, involving brain, vascular, or hormonal disturbance. Medical treatment for ED was either invasive or ineffective before the development of sildenafil, a selective PDE5 inhibitor. Other examples of PDE5 inhibitors include Tadalafil (Giovanni V F et al., Clin. Interv. Aging. 1 (2006) 439-449), and vardenafil (Markou S et al., Int. J. Impot. Res. 16 (2004) 470-478; Antonio M M et al., Clin. Interv. Aging 4 (2009) 463-472).

The FDA has approved these inhibitors as first-line treatment for male erectile dysfunction (MED). They raise the concentration of the crucial secondary messenger cyclic guanosine-3,5-monophosphate (cGMP), which controls various physiological processes. The level of intracellular cGMP is determined by the activities of the cyclase enzyme which produces it and the type-V phosphodiesterase (PDE-5) that degrades it.

PDE-5 inhibition can be used as a therapeutic approach for male ED as well as the treatment of cardiovascular diseases because it increases the level of cGMP (Ursula G and Gleiter C H, Eur. J. Med. Res. 29 (2002) 435-446; Sheila A D, Expert. Opin. Pharmacother. 6 (2005) 75-84).

Thus, new PDE-5 inhibitor compounds solving the aforementioned problems are desired.

SUMMARY

The present subject matter relates to treatment of erectile dysfunction and potential inhibition of the PDE5 enzyme using a series of 1,4-disubstituted piperidine derivatives containing arenesulfonyl and anilide groups. These derivatives exhibit potential inhibition of the PDE5 enzyme with suppression of rat's erectile dysfunction. These compounds have the general formulae (I), (II), (III) and (IV):

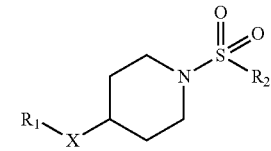

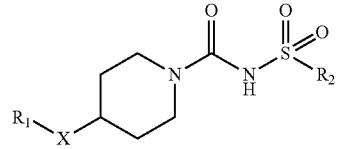

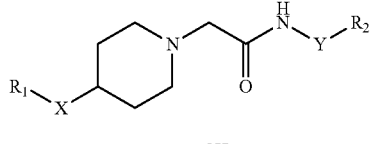

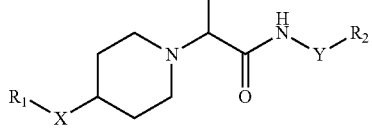

In certain embodiments of these compounds, $R_1$ can represent an alkyl or aryl group having alkyl, halogen, and/or alkoxy substituents thereon, whereas $R_2$ can represent an alkyl or aryl group having alkyl, halogen, alkoxy, and/or sulfonamide substituents thereon, optionally an acid hydrazide in which one hydrogen is substituted by an alkyl or aryl group having alkyl, halogen, alkoxy, and sulfonamide substituents. X and Y can each independently represent a non-alkyl or alkyl group.

The present subject matter further features a method for the synthesis of the compounds of formulae I and II comprising the steps of reacting 4-disubstituted piperidines with arenesulfonyl chloride or arenesulfonylisocyanate to form a compound having the formulae I or II. In another aspect, the present subject matter features a method for preparing a compound of the formulae III and IV comprising the steps of reacting 4-disubstituted piperidines with acyl chloride to form a compound having the formulae II and III.

The present subject matter also includes a method for inhibiting the PDE5 enzyme. In another aspect, the present subject matter includes a method for treating erectile dysfunction.

In an embodiment, the present subject matter relates to a compound having the formula A:

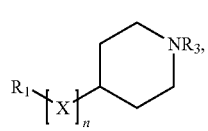

or a pharmaceutically acceptable salt, ester, stereoisomer, or solvate thereof, wherein:
 $R_1$ is selected from a group consisting of phenyl, benzyl, and methyl;
 $R_3$ is selected from a group consisting of $S(O)_2R_2$, $C(O)N(H)S(O)_2R_2$, $CH_2C(O)N(H)Y_mR_2$, and $CH(CH_3)C(O)N(H)Y_mR_2$;

X and Y are each independently a $C_1$-$C_6$ alkyl, such as methyl or ethyl;

m and n are each independently 0 or 1; and $R_2$ is selected from a group consisting of methyl, naphthyl, and phenyl optionally substituted with one, two, or three groups each independently selected from a group consisting of halide, alkyl, alkoxy, nitro, and sulfonamide groups.

In another embodiment, the present subject matter relates to a compound having the formula A:

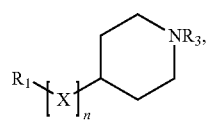

A or a pharmaceutically acceptable salt, ester, stereoisomer, or solvate thereof, wherein:

$R_1$ is selected from a group consisting of phenyl, benzyl, and methyl;

$R_3$ is selected from a group consisting of $S(O)_2R_2$, $C(O)N(H)S(O)_2R_2$, $CH_2C(O)N(H)Y_mR_2$, and $CH(CH_3)C(O)N(H)Y_mR_2$;

X is a $C_1$-$C_6$ alkyl, such as methyl or ethyl;

n is 0 or 1;

$R_2$ is selected from a group consisting of methyl, naphthyl, and a phenyl optionally substituted with one, two, or three groups each independently selected from a group consisting of halide, alkyl, alkoxy, nitro, and sulfonamide groups;

Y is a $C_1$-$C_6$ alkyl, such as methyl or ethyl; and m is 0 or 1.

In an embodiment, the present subject matter relates to a compound selected from the group consisting of:

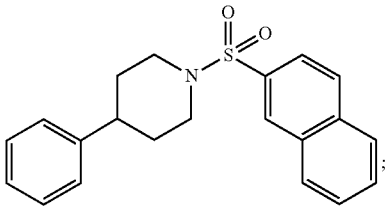
(C1)

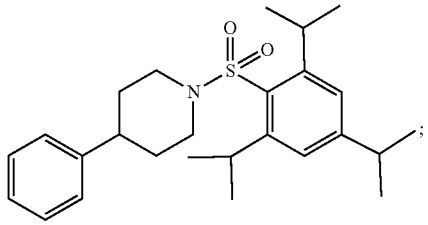
(C2)

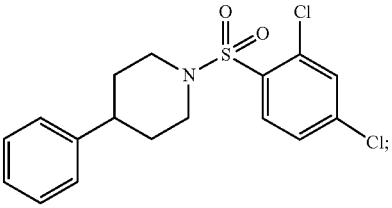
(C3)

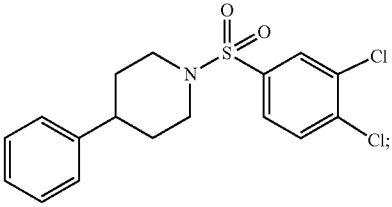
(C4)

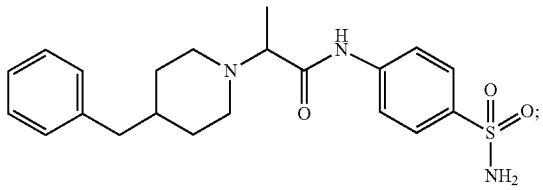
(C7)

(C9)

(C11)

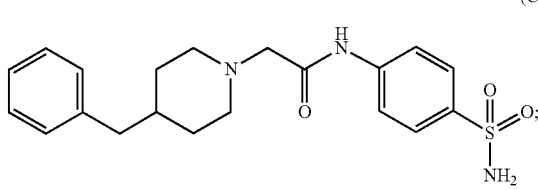
(C12)

(C13)

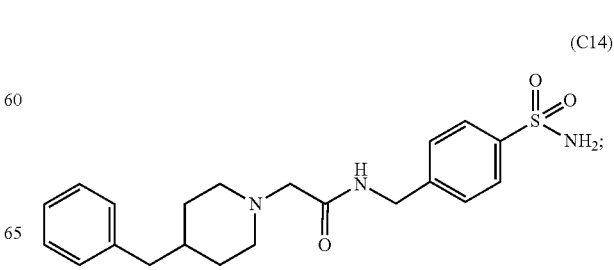
(C14)

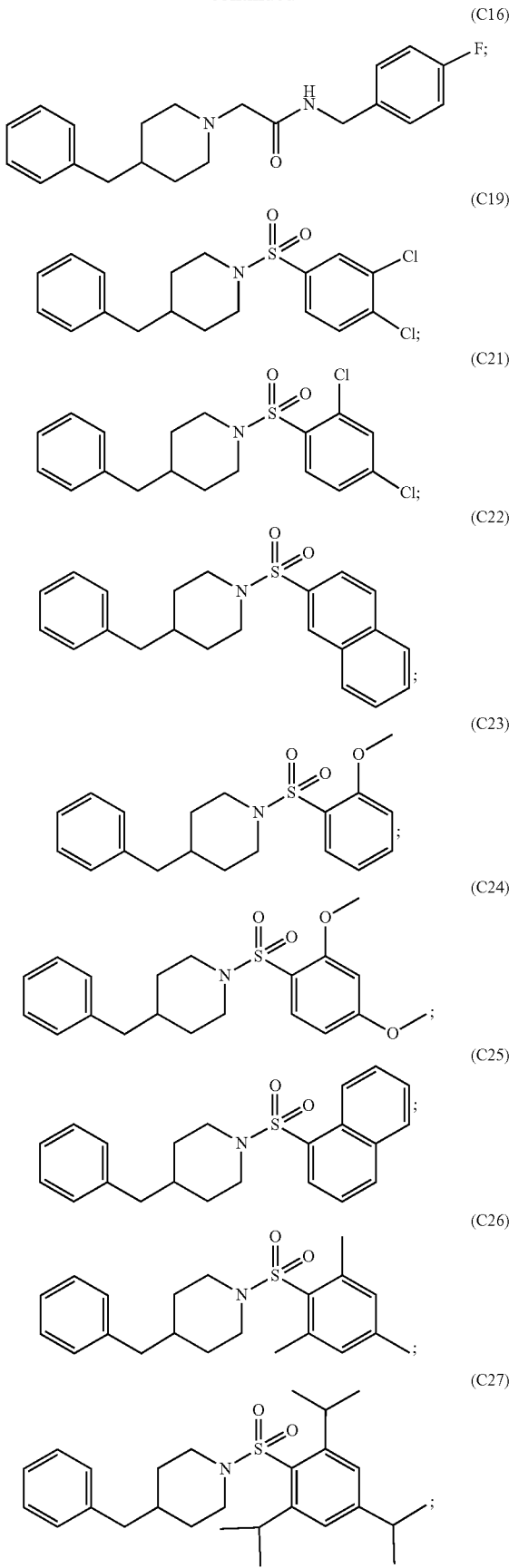

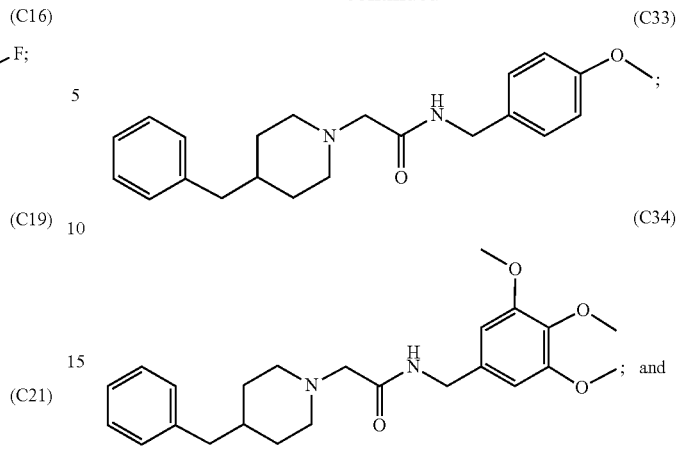

a pharmaceutically acceptable salt, ester, stereoisomer, or solvate thereof.

In an embodiment, the present subject matter relates to a process for the synthesis of the compounds of formula A, including a number of species or specific structures falling under structural formula A. Further contemplated herein are pharmaceutical compositions containing these compounds, as well as methods of inhibiting PDE5 enzyme activity and of treating various cancers by administering the present compounds to a patient in need thereof.

These and other features of the present subject matter will become readily apparent upon further review of the following specification.

DETAILED DESCRIPTION OF THE PREFERRED EMBODIMENTS

Figure 1A:
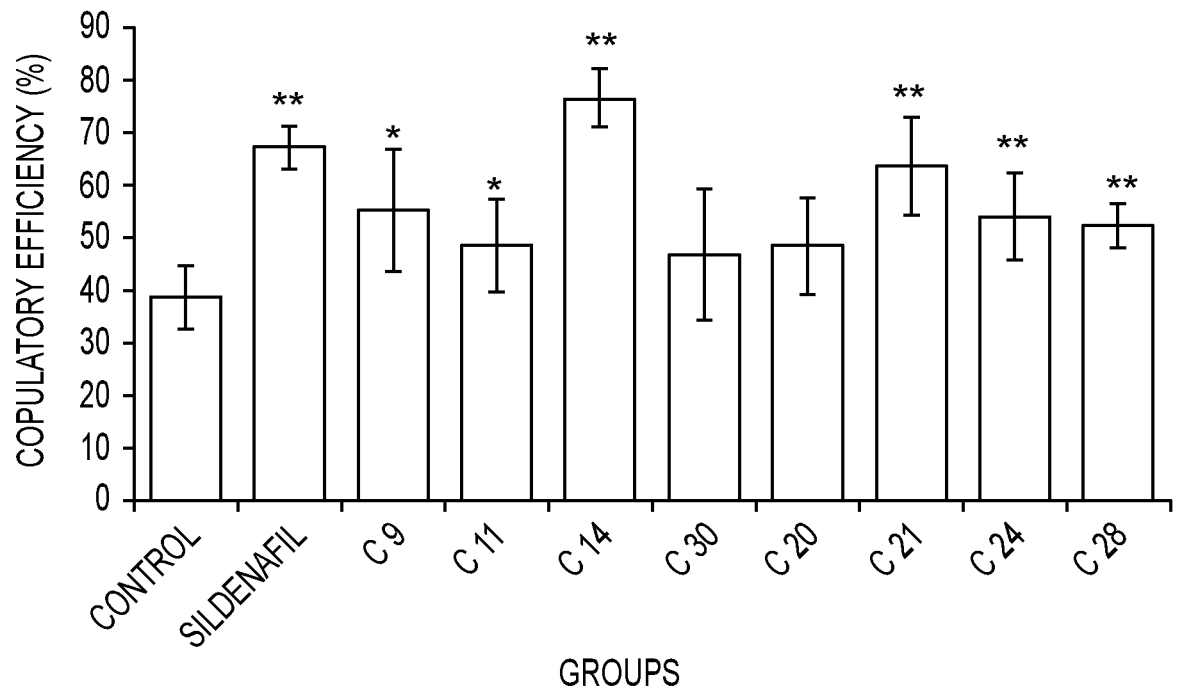
FIGS. 1A and 1B show the effect of sildenafil and synthesized compounds at 5 mg/kg on copulatory efficiency (FIG. 1A) and the mean intromission interval (FIG. 1B) of male rats. Copulatory efficiency (CE)=(IF/MF)×100, wherein IF is intromission frequence and MF is mount frequency. Mean intromission interval (MII)=EL/IF, wherein EL is ejaculation latency. Each value represents the mean of three independent experiments±SD. *P<0.05 and **P<0.01 versus control (Student's t-test).
Figure 1B:
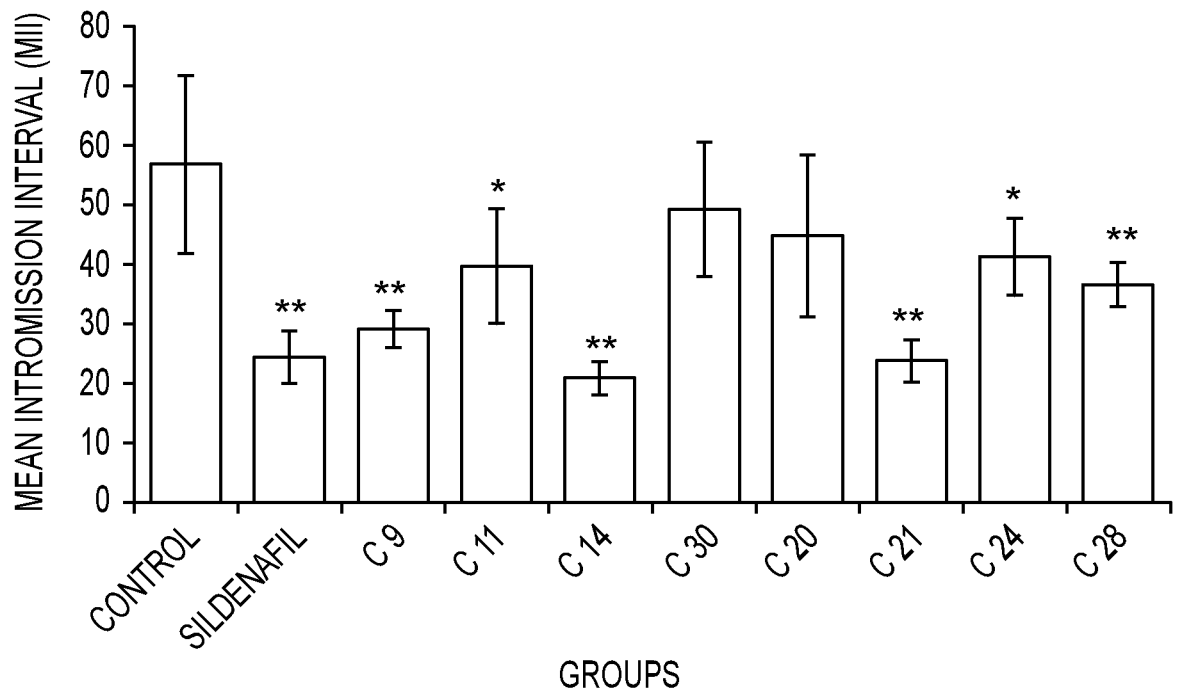
Figure 2A:
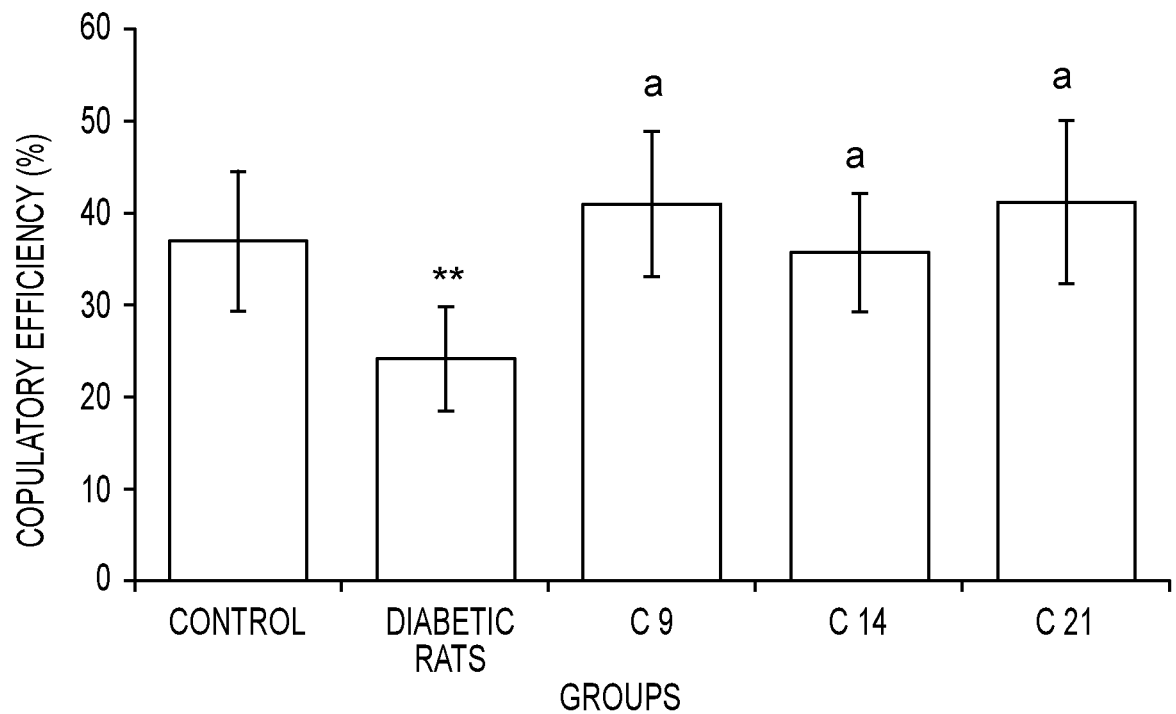
FIGS. 2A and 2B show the effect of the synthesized compounds C9, C14, and C21 (5 mg/kg/day for 14 days) on the copulatory efficiency (FIG. 2A) and the mean intromission interval (FIG. 2B) of male diabetic rats. Copulatory efficiency (CE)=(IF/MF)×100. Mean intromission interval (MII)=EL/IF. Each value represents the mean of three independent experiments±SD. **P<0.01 versus control and P<0.01 versus diabetic rats (Student's t-test).
Figure 2B:
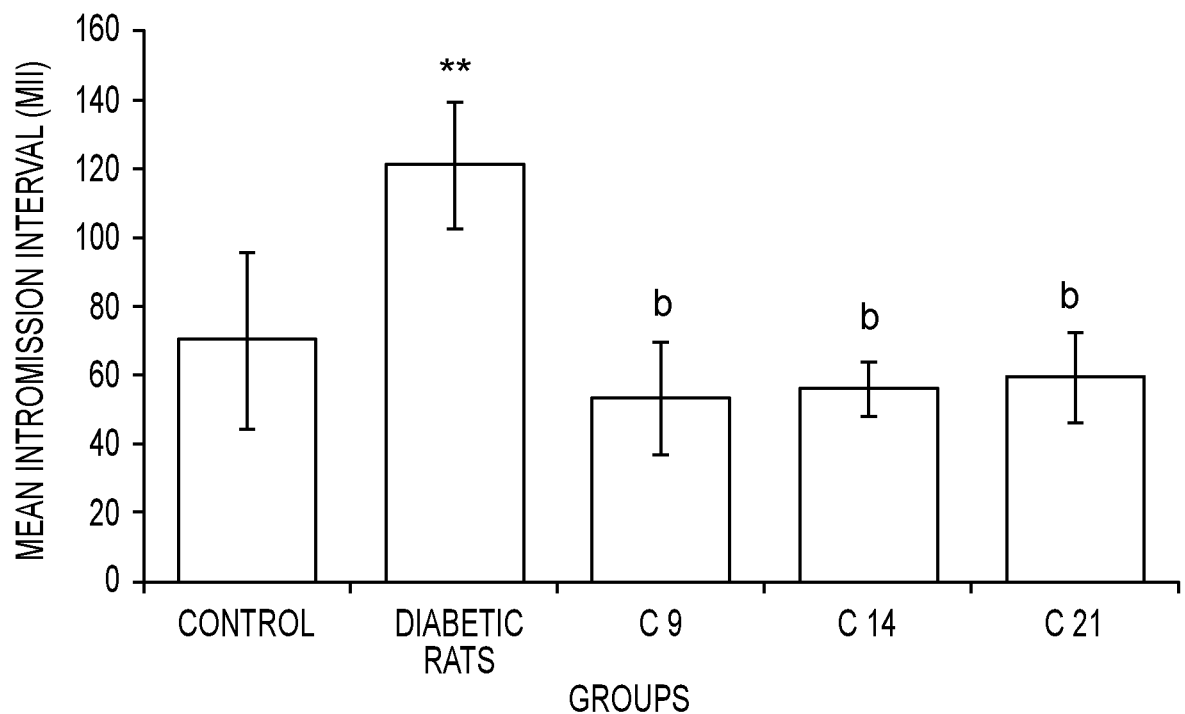

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo", "halide", or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms and can be referred to as a "lower alkyl group" or a "$C_1$-$C_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group) or 2 to 6 carbon atoms (i.e., $C_2$-$C_6$ alkenyl group). In some embodiments, alkenyl groups can be substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "substituted alkenyl" refers to an alkenyl group in which 1 or more (up to about 5, for example about 3) hydrogen atoms is replaced by a substituent independently selected from those listed above with respect to a substituted alkyl. Other alkenyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C6F5), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S-0 bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as cardiovascular diseases and/or erectile dysfunction.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a compound having the formula A:

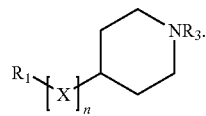

or a pharmaceutically acceptable salt, ester, stereoisomer, or solvate thereof, wherein:
$R_1$ is selected from a group consisting of phenyl, benzyl, and methyl;
$R_3$ is selected from a group consisting of $S(O)_2R_2$, $C(O)N(H)S(O)_2R_2$, $CH_2C(O)N(H)Y_mR_2$, and $CH(CH_3)C(O)N(H)Y_mR_2$;
X and Y are each independently a $C_1$-$C_6$ alkyl, such as methyl or ethyl;
n and m are independently 0 or 1; and
$R_2$ is selected from a group consisting of methyl, naphthyl, and phenyl optionally substituted with one, two, or three groups independently selected from halide, alkyl, alkoxy, nitro, and sulfonamide groups.

In a further embodiment, the present subject matter relates to compounds of formula A, wherein $R_1$ is phenyl, $R_3$ is $S(O)_2R_2$, $R_2$ is phenyl optionally substituted with one or more selected from halogens, alkyls, and alkoxies, and n is 0.

In yet another embodiment, the present subject matter relates to compounds of formula A, wherein $R_1$ is phenyl, X is $CH_2$, n is 1, $R_3$ is $S(O)_2R_2$, and $R_2$ is phenyl optionally substituted with one or more selected from halogen, alkyl, and alkoxy.

In another embodiment, the present subject matter relates to a compound of formula A, wherein $R_1$ is phenyl, X is $CH_2$, n is 1, $R_3$ is $CH_2C(O)N(H)Y_mR_2$, Y is $CH_2$, m is 1, and $R_2$ is phenyl optionally substituted with one or more selected from halogen, alkyl, alkoxy, and $SO_2NH_2$.

In still yet another embodiment, the present subject matter relates to compounds of formula A, wherein $R_1$ is phenyl, X is $CH_2$, n is 1, $R_3$ is $CH_2C(O)N(H)Y_mR_2$, m is 0, and $R_2$ is phenyl substituted with one or more $S(O)_2NH_2$. In an embodiment, $R_2$ is phenyl substituted with one $S(O)_2NH_2$.

In one embodiment, the present subject matter relates to a compound of formula A, wherein $R_1$ is phenyl, X is $CH_2$, n is 1, and $R_3$ is $CH(CH_3)C(O)N(H)Y_mR_2$.

In another embodiment, the present subject matter relates to a compound of formula A, wherein $R_1$ is phenyl, X is $CH_2$, n is 1, $R_3$ is $CH_2(CH_3)C(O)N(H)Y_mR_2$, m is 0, and $R_2$ is a phenyl substituted with $S(O)_2NH_2$.

In still yet another embodiment, the present subject matter relates to compounds of formula A, wherein $R_1$ is phenyl, X is $CH_2$, n is 1, $R_3$ is $CH_2(CH_3)C(O)N(H)Y_mR_2$, m is 0, and $R_2$ is a phenyl substituted with a halogen. In an embodiment, the halogen may be a fluorine.

In another embodiment, the present subject matter relates to a compound having the formula A:

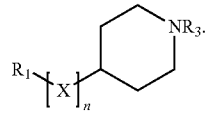

or a pharmaceutically acceptable salt, ester, stereoisomer, or solvate thereof, wherein:
$R_1$ is selected from a group consisting of phenyl, benzyl, and methyl;
$R_3$ is selected from a group consisting of $S(O)_2R_2$, $CH_2C(O)N(H)Y_mR_2$, and $CHCH_3CONHYR_2$;
X is a $C_1$-$C_6$ alkyl such as methyl or ethyl and n is 0 or 1;
$R_2$ is selected from a group consisting of methyl, naphthyl, and phenyl optionally substituted with one, two, or three groups each independently selected from halide, alkyl, alkoxy, nitro, and sulfonamide groups; and
Y is a $C_1$-$C_6$ alkyl such as methyl or ethyl and m is 0 or 1.

In an embodiment, the present subject matter relates to a compound selected from the group consisting of:

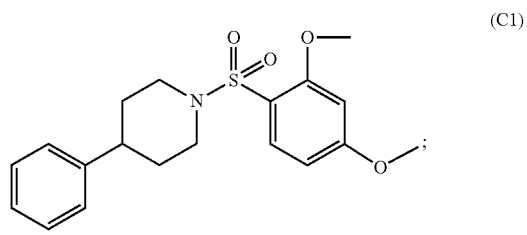
(C1)

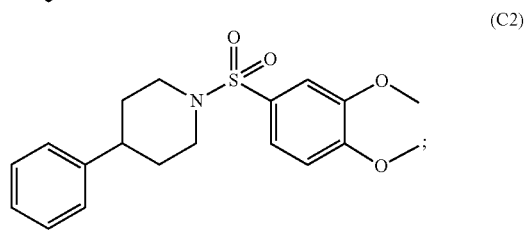
(C2)

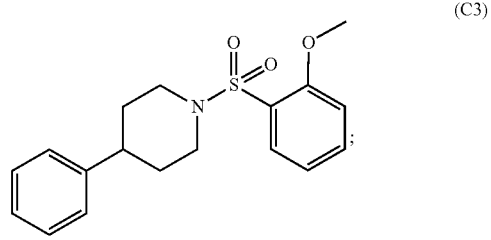
(C3)

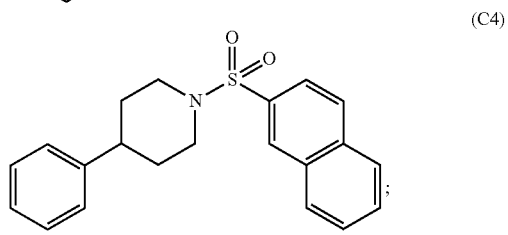
(C4)

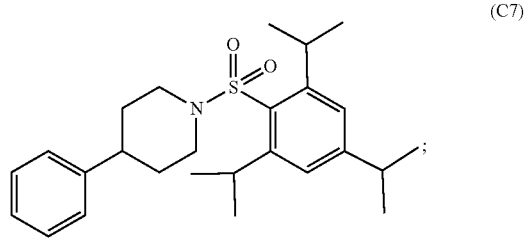
(C7)

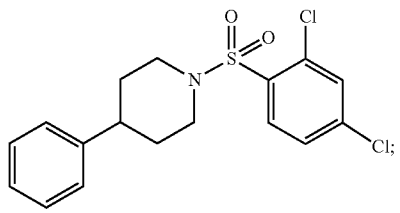 (C9)
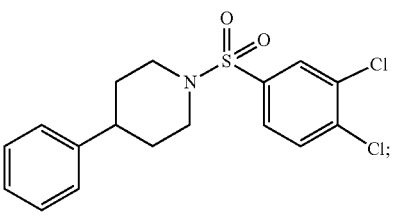 (C11)
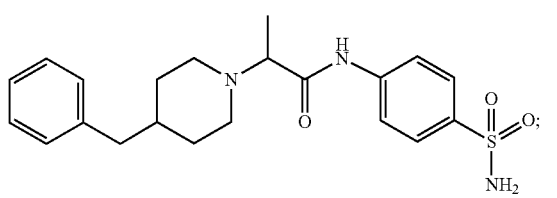 (C12)
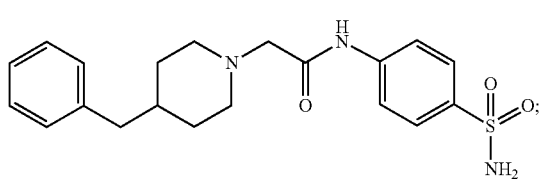 (C13)
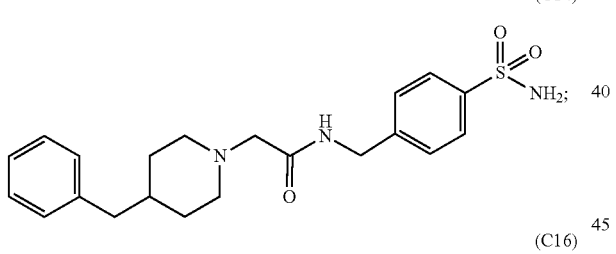 (C14)
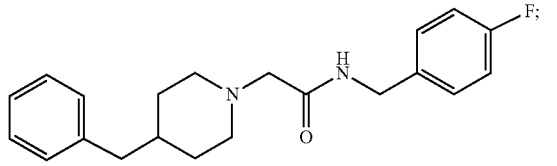 (C16)
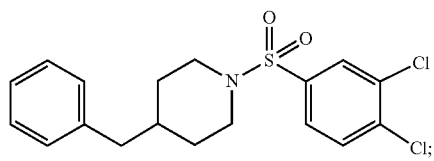 (C19)
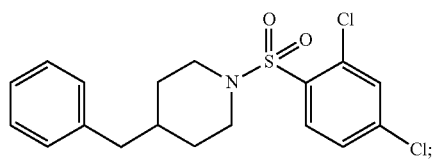 (C21)
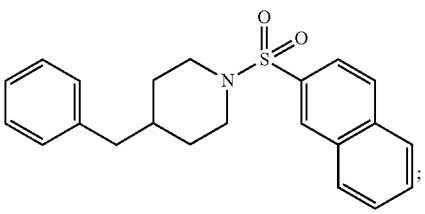 (C22)
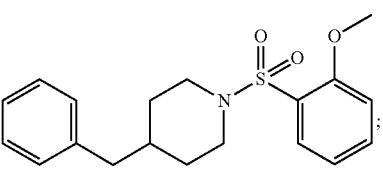 (C23)
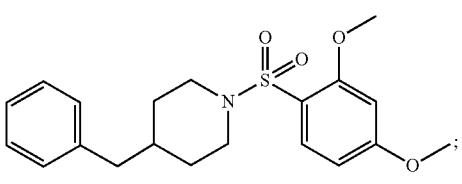 (C24)
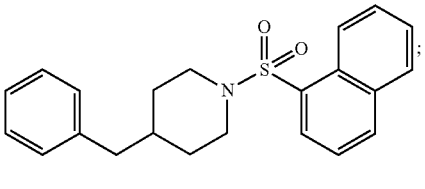 (C25)
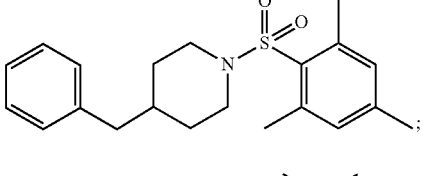 (C26)
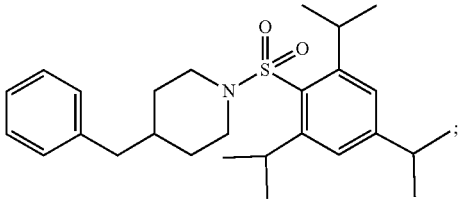 (C27)
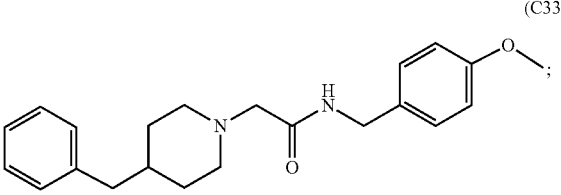 (C33)
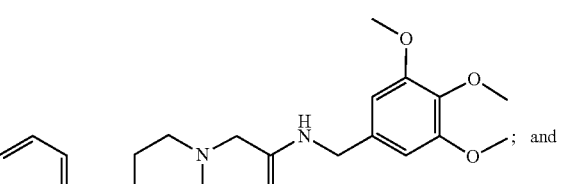 (C34)
; and
a pharmaceutically acceptable salt, ester, stereoisomer, or solvate thereof.

Said differently, the present subject matter can relate to compounds of formula I selected from the group consisting of:
1-((2,4-Dimethoxyphenyl)sulfonyl)-4-phenylpiperidine (C1);
1-((3,4-Dimethoxyphenyl)sulfonyl)-4-phenylpiperidine (C2);
1-((2-Methoxyphenyl)sulfonyl)-4-phenylpiperidine (C3);
1-((1-naphthyl)sulfonyl)-4-phenylpiperidine (C4);
1-((2,4,6-tri-isiopropylphenyl)sulfonyl)-4-phenylpiperidine (C7);
1-((2,4-Dichlorophenyl)sulfonyl)-4-phenylpiperidine (C9);
1-((3,4-Dichlorophenyl)sulfonyl)-4-phenylpiperidine (C11);
2-(4-Benzylpiperidin-1-yl)-N-(4-sulfamoylphenyl)-2-methylacetamide (C12);
2-(4-Benzylpiperidin-1-yl)-N-(4-sulfamoylphenyl)acetamide (C13);
2-(4-Benzylpiperidin-1-yl)-N-(4-sulfamoylbenzyl)acetamide (C14);
2-(4-Benzylpiperidin-1-yl)-N-(4-fluorobenzyl)acetamide (C16);
1-((3,4-Dichlorophenyl)sulfonyl)-4-Benzylpiperidine (C19);
1-((2,4-Dichlorophenyl)sulfonyl)-4-Benzylpiperidine (C21);
1-((1-naphthyl)sulfonyl)-4-Benzylpiperidine (C22);
1-((2-methoxyphenyl)sulfonyl)-4-Benzylpiperidine (C23);
1-((2,4-Dimethoxyphenyl)sulfonyl)-4-Benzylpiperidine (C24);
1-((2-naphthyl)sulfonyl)-4-Benzylpiperidine (C25);
1-((2,4,6-Trimethylphenyl)sulfonyl)-4-Benzylpiperidine (C26);
1-((2,4,6-Tri-isopropylphenyl)sulfonyl)-4-Benzylpiperidine (C27);
2-(4-Benzylpiperidin-1-yl)-N-(4-methoxybenzyl)acetamide (C33);
2-(4-Benzylpiperidin-1-yl)-N-(3,4,5-trimethoxybenzyl)acetamide (C34);
and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula A, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula A and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general synthetic pathway:

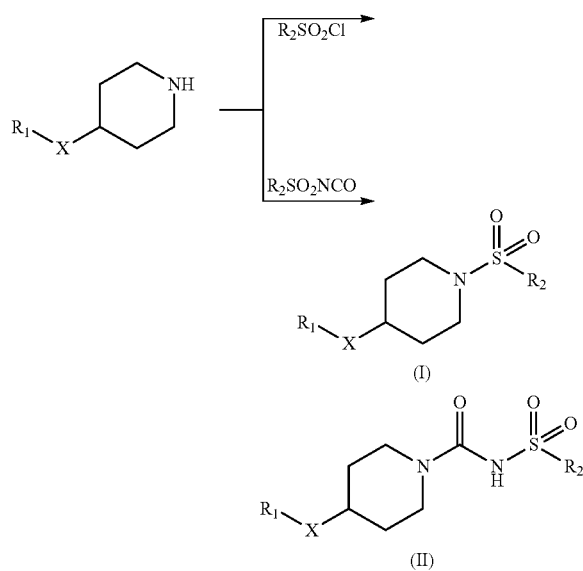

wherein:
R$_1$ represents phenyl, benzyl, or methyl;
X represents methyl or a non-attachable group (i.e., is absent); and
R$_2$ is methyl, naphthyl, or phenyl optionally substituted with one, two, or three groups that are each independently selected from halide, alkyl, alkoxy, and nitro groups.

Specifically, for these embodiments, synthesis commences with reacting 4-disubstituted piperidines with arenesulfonyl chloride in basic conditions to form the compound of formula I using the method published by Abdel-Aziz A M et al., E J Med Chem 46 (2011) 5487-5497, the contents of which are hereby incorporated by reference in their entirety, or reacted with arenesulfonylisocyanate in a basic environment to form said compound of formula II using the method published by El-Sherbeny M A et al., E J Med Chem 45 (2010) 689-697, the contents of which are hereby incorporated by reference in their entirety.

In this method, the arenesulfonyl chloride and arenesulfonylisocyanate useful in the present subject matter can include, but are not limited to, 2-methoxybenzenesulfonyl chloride, 2,4-dimethoxybenzenesulfonyl chloride, 3,4-dimethoxybenzenesulfonyl chloride, 2,4-dichlorobenzenesulfonyl chloride, 3,4-dichlorobenzenesulfonyl chloride, 2,4-difluorobenzenesulfonyl chloride, 2,4,6-trichlorobenzenesulfonyl chloride, 2,4,6-triisopropylbenzenesulfonyl chloride, 2,4,6-trimethylbenzenesulfonyl chloride, 2,3,4,5,6-pentamethylbenzenesulfonyl chloride, 2-naphthylsulfonyl chloride, 1-naphthylsulfonyl chloride, phenylsulfonyl isocyanate, 4-methoxybenzenesulfonyl isocyanate, 4-methylbenzenesulfonyl isocyanate, and 4-chlorobenzenesulfonyl isocyanate.

According to another embodiment of the present disclosure, the present compounds of formulae III and IV can be prepared by the following scheme:

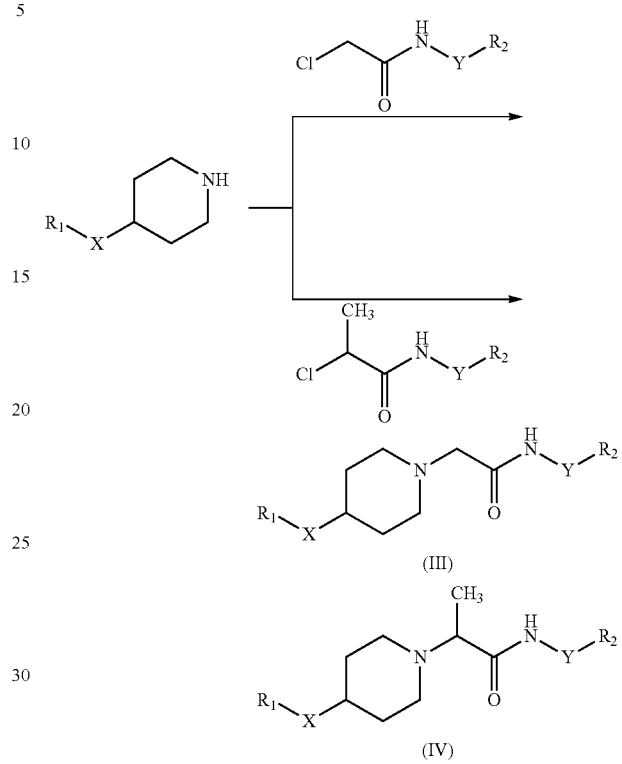

wherein:
R$_1$ represents phenyl, benzyl, or methyl;
X and Y independently represent methyl, ethyl, or another lower alkyl in multiples of 1 or 0; and
R$_2$ is phenyl optionally substituted with one, two, or three groups that are each independently selected from halide, alkyl, alkoxy, nitro or sulfonamide groups.

According to the method of the present synthesis of a compound of formulae III and IV, 4-disubstituted piperidines are reacted with acetanilide chloride in a basic condition to form a compound of formula III or reacted with propanilide chloride in a basic environment to create a compound of formula IV.

In this method, the acetanilide chloride and propanilide chloride used in the present method can include, but are not limited to, 2-chloro-N-(4-sulfamoylphenyl)acetamide, 2-chloro-N-(4-sulfamoylbenzyl)acetamide, 2-chloro-N-(4-sulfamoylphenyl)propanamide, 2-chloro-N-(4-sulfamoylbenzyl)propanamide, 2-chloro-N-phenylacetamide, substituted 2-chloro-N-phenylacetamide, N-benzyl-2-chloropropanamide, and substituted N-benzyl-2-chloropropanamide.

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for erectile dysfunction. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of cancer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of diseases such as erectile dysfunction. Similarly, the present compounds can be used to inhibit PDE5 enzyme activity in a patient.

In another embodiment of the present subject matter, the aforementioned compound derivatives demonstrated in vitro (PDE5) inhibition activities Accordingly, the present subject matter relates to methods of treating an erectile dysfunction in a patient by administering one or more of the compounds presented herein to a patient in need thereof. In certain embodiments, the cardiovascular disease can be treated by the PDE5 inhibitors listed as vasodilators.

Accordingly, in an embodiment of the present subject matter, the 1,4-disubstituted piperidine derivatives compounds as described herein engaged for in vitro study towards PDE5 inhibition can display an $IC_{50}$ with a nano to micromolar concentration range when exposed to a period of at least 30 minutes. The $IC_{50}$ values range from 39.44±0.76 to 874.35±17.06 nM.

The present subject matter further relates to a method of treating or preventing a condition comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used. Similarly, one or more of the present compounds can be used in combination therapy with one or more additional active agents.

The following examples relate to various methods of manufacturing certain specific compounds as described herein. All compound numbers expressed herein are with reference to the synthetic pathway figures shown above.

EXAMPLES

Example 1

A General Method for Synthesis of 4-Phenylpiperidine and 4-Benzylpiperidine Containing Arenesulfonyl Fragments (Formula I)

A mixture of 4-phenylpiperidine or 4-benzylpiperidine (1.0 mmol) (Scheme 1) and $K_2CO_3$ (152 mg, 1.1 mmol) was stirred in acetone (20 mL) at room temperature for 20 min. The appropriate arenesulfonyl chloride (1.2 mmol) in acetone (5 mL) was added to the resulting mixture, and the reaction mixture was further stirred at room temperature for 24 h. The separated solid was then filtered, washed with cold water, dried and crystallized from the appropriate solvent.

Example 2

1-((2,4-Dimethoxyphenyl)sulfonyl)-4-phenylpiperidine (C1)

Yield, 98%; mp 191-193° C. (MeOH/$CH_2Cl_2$); IR(KBr) v max/cm$^{-1}$: 1326, 1155 ($SO_2$). $^1$H NMR (500 MHz, DMSO) δ 7.68 (d, J=8.8 Hz, 1H), 7.28 (t, J=7.5 Hz, 2H), 7.23-7.14 (m, 3H), 6.75 (d, J=2.4 Hz, 1H), 6.66 (dd, J=8.9, 2.3 Hz, 1H), 3.87 (d, J=14.4 Hz, 6H), 3.75 (dt, J=12.3, 2.7 Hz, 2H), 2.58 (qd, J=12.5, 3.0 Hz, 3H), 1.89-1.71 (m, 2H), 1.58 (qd, J=12.6, 4.1 Hz, 2H).

$^{13}$C NMR (126 MHz, DMSO) δ 164.86, 158.86, 145.91, 133.09, 128.87, 127.13, 126.69, 118.29, 105.57, 99.98, 56.56, 56.26, 46.64, 41.44, 33.09. MS m/z (%): 361.21 (10.1%).

Example 3

1-((3,4-Dimethoxyphenyl)sulfonyl)-4-phenylpiperidine (C2)

Yield, 94%; mp 207-209° C. (MeOH/$CH_2Cl_2$); IR(KBr) v max/cm$^{-1}$: 1303, 1135 ($SO_2$). $^1$H NMR (500 MHz, DMSO) δ 7.36 (dd, J=8.4, 2.2 Hz, 1H), 7.28 (t, J=7.6 Hz, 2H), 7.20 (dq, J=14.0, 6.9 Hz, 5H), 3.95-3.84 (m, 6H), 3.77 (d, J=11.7 Hz, 2H), 2.50-2.42 (m, 1H), 2.37-2.26 (m, 2H), 1.89-1.78 (m, 2H), 1.68 (td, J=12.6, 4.2 Hz, 2H).

$^{13}$C NMR (126 MHz, DMSO) δ 152.93, 149.19, 145.73, 128.85, 127.14, 121.80, 111.89, 110.59, 56.37, 47.03, 41.04, 32.49. MS m/z (%): 361.17 (18.2%).

Example 4

1-((2-Methoxyphenyl)sulfonyl)-4-phenylpiperidine (C3)

Yield, 89%; mp 173-175° C. (EtOH/CH$_2$Cl$_2$); IR(KBr) v max/cm$^{-1}$: 1353, 1150 (SO$_2$). $^1$H NMR (500 MHz, DMSO) δ 7.68 (d, J=8.6 Hz, 2H), 7.31-7.21 (m, 2H), 7.17-7.13 (m, 3H), 7.11 (d, J=8.8 Hz, 2H), 3.87 (d, J=1.0 Hz, 3H), 3.78 (dq, J=11.2, 2.2 Hz, 2H), 2.48-2.36 (m, 1H), 2.29 (td, J=12.0, 2.6 Hz, 2H), 1.88-1.78 (m, 2H), 1.70 (qd, J=12.6, 4.0 Hz, 2H).
$^{13}$C NMR (126 MHz, DMSO) δ 163.12, 145.33, 129.98, 128.69, 127.53, 126.93, 126.60, 114.69, 55.97, 46.89, 41.31, 32.51. MS m/z (%): 331.27 (15.6%).

Example 5

1-(Mesitylsulfonyl)-4-phenylpiperidine (C6)

Yield, 85%; mp 157-159° C. (MeOH/CH$_2$Cl$_2$); IR(KBr) v max/cm$^{-1}$: 1286, 1147 (SO$_2$). $^1$H NMR (500 MHz, DMSO) δ 7.56-6.97 (m, 7H), 3.57 (d, J=12.3 Hz, 2H), 2.95-2.75 (m, 3H), 2.59 (s, 6H), 2.28 (s, 3H), 1.81 (d, J=13.2 Hz, 2H), 1.67-1.49 (m, 2H).
$^{13}$C NMR (126 MHz, DMSO) δ 145.72, 142.81, 140.09, 132.34, 132.23, 128.87, 127.08, 126.73, 44.91, 41.45, 32.62, 22.87, 20.90. MS m/z (%): 343.38 (11.0%).

Example 6

1-((2,4-Dichlorophenyl)sulfonyl)-4-phenylpiperidine (C9)

Yield, 90%; mp 175-177° C. (MeOH/CH$_2$Cl$_2$); IR(KBr) v max/cm$^{-1}$: 1342, 1162 (SO$_2$). $^1$H NMR (500 MHz, DMSO) δ 7.99 (dd, J=8.5, 1.1 Hz, 1H), 7.72 (d, J=2.0 Hz, 1H), 7.55 (dd, J=8.6, 2.1 Hz, 1H), 7.25 (t, J=7.6 Hz, 2H), 7.19-7.12 (m, 3H), 3.86 (ddd, J=12.4, 4.4, 2.3 Hz, 2H), 2.81 (td, J=12.5, 2.4 Hz, 2H), 2.60 (tt, J=12.3, 3.6 Hz, 1H), 1.84 (dt, J=13.5, 2.8 Hz, 2H), 1.65 (qd, J=12.9, 3.9 Hz, 2H).
$^{13}$C NMR (126 MHz, DMSO) δ 145.27, 138.98, 135.18, 133.30, 132.85, 132.01, 128.72, 128.07, 126.90, 126.64, 46.38, 41.36, 32.94. MS m/z (%): 369.31 (17.8,0%).

Example 7

1-((3,4-Dichlorophenyl)sulfonyl)-4-phenylpiperidine (C11)

Yield, 92%; mp 217-219° C. (EtOH/CH$_2$Cl$_2$); IR(KBr) v max/cm$^{-1}$: 1341, 1165 (SO$_2$). $^1$H NMR (500 MHz, CDCl$_3$) δ 7.92 (d, J=1.8 Hz, 1H), 7.69-7.63 (m, 2H), 7.34 (t, J=7.6 Hz, 2H), 7.24 (d, J=7.4 Hz, 1H), 7.18 (d, J=7.0 Hz, 2H), 3.98 (d, J=11.5 Hz, 2H), 2.60-2.37 (m, 3H), 2.03-1.80 (m, 4H).
$^{13}$C NMR (126 MHz, CDCl$_3$) δ 144.58, 137.65, 136.23, 133.86, 131.16, 129.50, 128.69, 126.75, 126.74, 126.69, 46.88, 41.73, 32.52. MS m/z (%): 369.29 (14.90%).

Example 8

4-Benzyl-1-((3,4-dichlorophenyl)sulfonyl)piperidine (C19)

Yield, 95%; mp 166-168° C. (EtOH/CH$_2$Cl$_2$); IR(KBr) v max/cm$^{-1}$: 1340, 1164 (SO$_2$). $^1$H NMR (500 MHz, DMSO) δ 7.91 (dd, J=5.3, 3.1 Hz, 2H), 7.68 (dd, J=8.4, 2.1 Hz, 1H), 7.26 (t, J=7.5 Hz, 2H), 7.18 (d, J=7.3 Hz, 1H), 7.12 (d, J=7.0 Hz, 2H), 3.64 (d, J=12.4 Hz, 2H), 2.48 (d, J=7.0 Hz, 2H), 2.27 (t, J=12.0 Hz, 2H), 1.57 (ddd, J=40.9, 13.4, 6.2 Hz, 3H), 1.18 (qd, J=12.5, 4.3 Hz, 2H).
$^{13}$C NMR (126 MHz, DMSO) δ 140.20, 136.67, 132.88, 132.21, 129.44, 129.39, 128.60, 127.95, 126.32, 46.43, 42.04, 36.41, 31.11. MS m/z (%): 383.25 (13.9%).

Example 9

4-Benzyl-1-((2,4-dichlorophenyl)sulfonyl)piperidine (C21)

Yield, 93%; mp 125-127° C. (EtOH/CH$_2$Cl$_2$); IR(KBr) v max/cm$^{-1}$: 1340, 1164 (SO$_2$). $^1$H NMR (500 MHz, CDCl$_3$) δ 7.94 (ddd, J=9.2, 4.3, 2.1 Hz, 1H), 7.53-7.46 (m, 1H), 7.37-7.31 (m, 1H), 7.24 (dtt, J=6.1, 4.0, 2.0 Hz, 2H), 7.17 (tq, J=5.1, 1.7 Hz, 1H), 7.12-7.05 (m, 2H), 3.86-3.73 (m, 2H), 2.74-2.60 (m, 2H), 2.54-2.43 (m, 2H), 1.66 (d, J=13.4 Hz, 2H), 1.58 (tt, J=7.3, 3.6 Hz, 1H), 1.27 (dd, J=16.5, 8.9 Hz, 2H).
$^{13}$C NMR (126 MHz, CDCl$_3$) δ 139.66, 139.17, 135.20, 133.15, 133.14, 132.87, 131.83, 129.02, 128.44, 128.30, 127.22, 126.08, 45.99, 45.93, 45.91, 42.68, 37.44, 37.43, 31.66, 8.69. MS m/z (%): 383.25 (13.9%).

Example 10

4-Benzyl-1-((2-methoxyphenyl)sulfonyl)piperidine (C23)

Yield, 91%; mp 95-97° C. (MeOH/CH$_2$Cl$_2$); IR(KBr) v max/cm$^{-1}$: 1337, 1152 (SO$_2$). $^1$H NMR (500 MHz, DMSO) δ 7.76-7.57 (m, 2H), 7.37-7.21 (m, 3H), 7.13 (td, J=15.0, 7.4 Hz, 4H), 3.85 (s, 3H), 3.57 (d, J=11.7 Hz, 2H), 2.45 (d, J=7.3 Hz, 1H), 2.17-1.99 (m, 2H), 1.57 (d, J=13.1 Hz, 3H), 1.49-1.38 (m, 1H), 1.32-1.09 (m, 2H).
$^{13}$C NMR (126 MHz, DMSO) δ 163.05, 140.23, 130.06, 129.37, 128.59, 127.48, 126.29, 114.88, 56.14, 46.52, 42.14, 36.69, 31.14. MS m/z (%): 345.40 (11.6%).

Example 11

4-Benzyl-1-(mesitylsulfonyl)piperidine (C26)

Yield, 88%; mp 70-72° C. (EtOH/CH$_2$Cl$_2$); IR(KBr) v max/cm$^{-1}$: 1289, 1151 (SO$_2$). $^1$H NMR (500 MHz, CDCl$_3$) δ 7.29 (t, J=7.4 Hz, 2H), 7.21 (t, J=7.4 Hz, 1H), 7.13 (d, J=7.0 Hz, 2H), 6.96 (s, 2H), 3.58 (d, J=12.2 Hz, 2H), 2.72 (td, J=11.1, 3.4 Hz, 2H), 2.64 (s, 6H), 2.55 (d, J=7.0 Hz, 2H), 2.32 (s, 3H), 1.67 (ddt, J=21.6, 11.2, 3.7 Hz, 3H), 1.31-1.20 (m, 2H). $^{13}$C NMR (126 MHz, CDCl$_3$) δ 142.38, 140.43, 139.90, 131.94, 131.88, 129.06, 128.32, 126.07, 44.43, 42.85, 37.78, 31.45, 22.84, 20.98. MS m/z (%): 357.11 (20.3%).

Example 12

General method for synthesis of 4-phenylpiperidine and 4-benzylpiperidine containing anilide fragments (Formula III)

A mixture of 4-benzylpiperidine (1.0 mmol) and K$_2$CO$_3$ (1.2 mmol) was stirred in DMF (10 mL) at room temperature for 20 min. An appropriate acyl chloride (1.1 mmol) in DMF (5 mL) was added to the resulting mixture, and the reaction mixture was further stirred at room temperature for 24 h. The separated solid was then filtered, washed with cold water, dried and crystallized from the appropriate solvent.

Example 13

2-(4-Benzylpiperidin-1-yl)-N-(4-sulfamoylbenzyl) acetamide (C14)

Yield, 79%; mp 148-150° C. (MeOH); IR(KBr) v max/cm$^{-1}$: 3360 (NH), 1685 (C=O), 1325, 1161 (SO$_2$). $^1$H NMR (500 MHz, DMSO) δ 8.35 (t, J=6.3 Hz, 1H), 7.79 (d, J=8.5 Hz, 2H), 7.43 (d, J=8.4 Hz, 2H), 7.28 (t, J=7.5 Hz, 3H), 7.23-7.11 (m, 4H), 4.37 (d, J=6.3 Hz, 2H), 2.94 (s, 2H), 2.79 (d, J=11.6 Hz, 2H), 2.50 (s, 2H), 1.99 (t, J=11.6 Hz, 2H), 1.57-1.43 (m, 3H), 1.29 (qd, J=11.9, 3.9 Hz, 2H).

$^{13}$C NMR (126 MHz, DMSO) δ 170.41, 144.38, 143.07, 140.77, 129.47, 129.44, 128.61, 128.53, 127.94, 126.22, 126.12, 62.22, 54.12, 42.88, 42.04, 37.37, 32.07. MS m/z (%): 401.41 (30.3%).

Example 14

2-(4-Benzylpiperidin-1-yl)-N-(4-methoxyphenyl) acetamide (C15)

Yield, 81%; mp 61-63° C. (MeOH); IR(KBr) v max/cm$^{-1}$: 3341 (NH), 1659 (C=O). $^1$H NMR (500 MHz, DMSO) δ 9.49 (s, 1H), 7.54 (d, J=9.0 Hz, 2H), 7.28 (dt, J=5.9, 2.0 Hz, 2H), 7.17 (dt, J=7.8, 1.4 Hz, 3H), 6.88 (d, J=9.0 Hz, 2H), 3.73 (s, 3H), 3.03 (s, 2H), 2.87-2.78 (m, 2H), 2.48 (d, J=7.1 Hz, 1H), 2.06 (td, J=11.6, 2.3 Hz, 2H), 1.55 (dd, J=12.7, 3.6 Hz, 2H), 1.50 (dt, J=11.1, 3.2 Hz, 1H), 1.31 (qd, J=11.9, 3.9 Hz, 2H), 1.05 (qd, J=12.0, 4.0 Hz, 1H).

$^{13}$C NMR (126 MHz, DMSO) δ 168.50, 155.80, 140.82, 132.21, 129.47, 129.44, 128.60, 128.55, 126.21, 126.16, 121.49, 62.68, 55.65, 53.91, 42.85, 37.42, 32.10. MS m/z (%): 338.28 (12.6%).

Example 15

2-(4-Benzylpiperidin-1-yl)-N-(4-fluorobenzyl)acetamide (C16)

Yield, 84%; mp 72-74° C. (MeOH); IR(KBr) v max/cm$^{-1}$: 3374 (NH), 1660 (C=O). $^1$H NMR (500 MHz, DMSO) δ 8.23 (s, 1H), 7.21 (d, J=66.8 Hz, 9H), 4.73-4.13 (m, 2H), 3.20-2.67 (m, 5H), 1.99 (t, J=18.7 Hz, 2H), 1.80-0.89 (m, 6H).

$^{13}$C NMR (126 MHz, DMSO) δ 170.15, 140.76, 136.51, 129.63, 129.43, 128.59, 126.20, 115.46, 115.29, 62.24, 54.09, 42.89, 41.62, 37.38, 32.08. MS m/z (%): 340.20 (15.0%).

Example 16

2-(4-Benzylpiperidin-1-yl)-N-(4-methoxybenzyl) acetamide (C33)

Yield, 86%; mp 89-91° C. (MeOH); IR(KBr) v max/cm$^{-1}$: 3381 (NH), 1655 (C=O). $^1$H NMR (500 MHz, DMSO) δ 8.27 (s, 1H), 7.26 (t, J=7.5 Hz, 2H), 7.20-7.10 (m, 5H), 6.85 (d, J=8.6 Hz, 2H), 4.24 (d, J=5.1 Hz, 2H), 3.73 (s, 3H), 2.90 (s, 2H), 2.77 (d, J=11.6 Hz, 2H), 2.49 (d, J=6.9 Hz, 2H), 1.99 (td, J=11.6, 2.3 Hz, 2H), 1.59-1.42 (m, 3H), 1.26 (qd, J=11.8, 3.9 Hz, 2H).

$^{13}$C NMR (126 MHz, DMSO) δ 169.90, 169.83, 158.62, 140.67, 132.02, 132.01, 129.34, 128.90, 128.49, 126.11, 114.04, 62.25, 62.23, 55.42, 54.12, 42.92, 41.78, 41.67, 37.37, 32.10. MS m/z (%): 352.31 (19.9%).

Example 17

In Vitro Phosphodiesterase Type 5 (PDE5) Inhibition Assay

Phosphodiesterase type 5 (PDE5) inhibition assay of compounds of formula I, III, and IV and the reference drug sildenafil were performed according to the manufacturer's instruction. Briefly, Black 96-well non-binding plates with wells were filled with 5 µ/mL of purified PDE5 from BPS Biosciences. The protein was treated with the substance or the vehicle control immediately, and each assay received 50 nM TAMRAcGMP (Molecular Devices). 1.5 hours at 30° C. were spent incubating the plates. The plates were then incubated for an additional 30 minutes at 30° C. with IMAP FP Phosphodiesterase Evaluation Assay (Molecular Devices) binding reagent added to each well. FP was measured using a Biotek Synergy 4 plate reader under the manufacturer's recommendations.

Compounds C9, C11, C20, C21, C24, and C28 were the most potent PDE5 inhibitors (47.9, 56.7, 63.3, 41.2, 56.3, and 56.5 nM, respectively) in a series I. Compounds C14 and C30 were the most potent PDE5 inhibitors (39.44 and 59.0 nM, respectively) in a series 111.

TABLE 1

| Comd. NO. | Chemical Structure | IC$_{50}$ (nM) | Formulae |
|---|---|---|---|
| C1 | 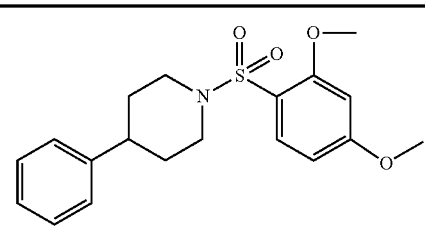 | 106.17 ± 2.07 | I |

TABLE 1-continued

| Comd. NO. | Chemical Structure | IC$_{50}$ (nM) | Formulae |
|---|---|---|---|
| C2 | 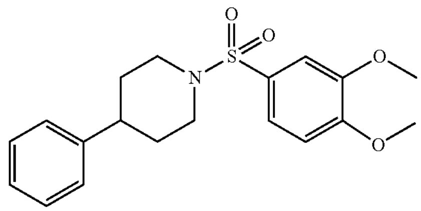 [SMILES: COc1ccc(S(=O)(=O)N2CCC(c3ccccc3)CC2)cc1OC] | 185.08 ± 3.61 | I |
| C3 | 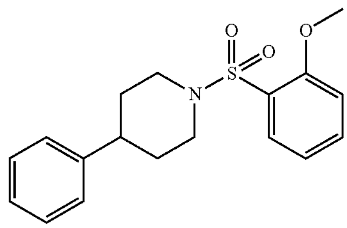 [SMILES: COc1ccccc1S(=O)(=O)N1CCC(c2ccccc2)CC1] | 85.23 ± 1.66 | I |
| C4 | 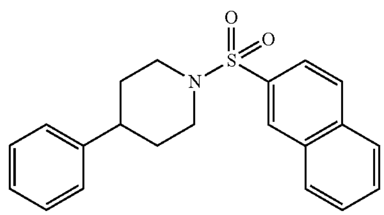 [SMILES: O=S(=O)(c1ccc2ccccc2c1)N1CCC(c2ccccc2)CC1] | 434.84 ± 8.48 | I |
| C5 | 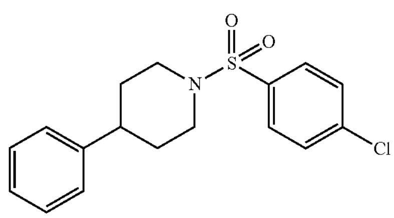 [SMILES: O=S(=O)(c1ccc(Cl)cc1)N1CCC(c2ccccc2)CC1] | 675.39 ± 13.18 | I |
| C6 | 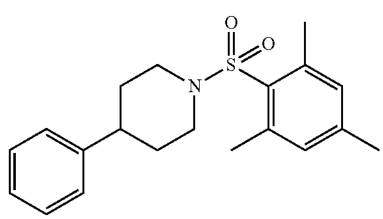 [SMILES: Cc1cc(C)c(S(=O)(=O)N2CCC(c3ccccc3)CC2)c(C)c1] | 295.81 ± 5.77 | I |
| C7 | 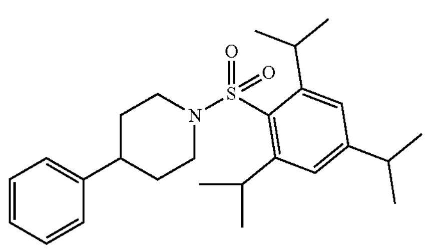 [SMILES: CC(C)c1cc(C(C)C)c(S(=O)(=O)N2CCC(c3ccccc3)CC2)c(C(C)C)c1] | 519.54 ± 10.14 | I |
| C8 | 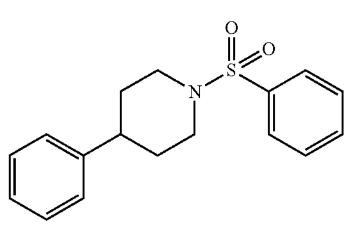 [SMILES: O=S(=O)(c1ccccc1)N1CCC(c2ccccc2)CC1] | 54.19 ± 1.057 | I |

TABLE 1-continued

| Comd. NO. | Chemical Structure | IC$_{50}$ (nM) | Formulae |
|---|---|---|---|
| C9 | 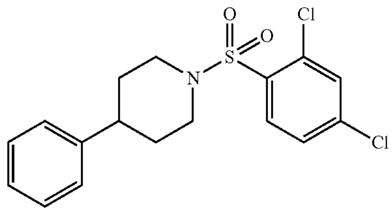 [SMILES: O=S(=O)(c1ccc(Cl)cc1Cl)N1CCC(c2ccccc2)CC1] | 47.94 ± 0.93 | I |
| C10 | 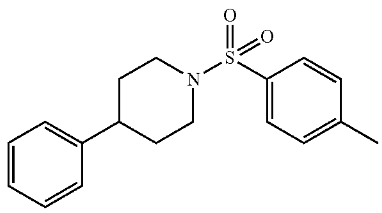 [SMILES: Cc1ccc(S(=O)(=O)N2CCC(c3ccccc3)CC2)cc1] | 133.08 ± 2.59 | I |
| C11 | 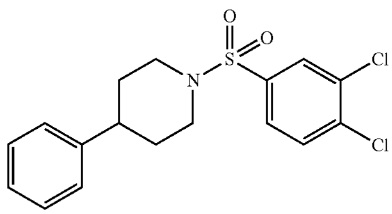 [SMILES: O=S(=O)(c1ccc(Cl)c(Cl)c1)N1CCC(c2ccccc2)CC1] | 56.76 ± 1.10 | I |
| C12 | 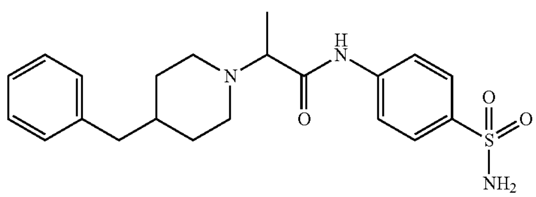 [SMILES: CC(C(=O)Nc1ccc(S(N)(=O)=O)cc1)N1CCC(Cc2ccccc2)CC1] | 874.35 ± 17.06 | IV |
| C13 | 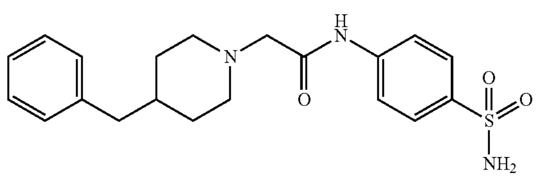 [SMILES: NS(=O)(=O)c1ccc(NC(=O)CN2CCC(Cc3ccccc3)CC2)cc1] | 221.34 ± 4.32 | III |
| C14 | 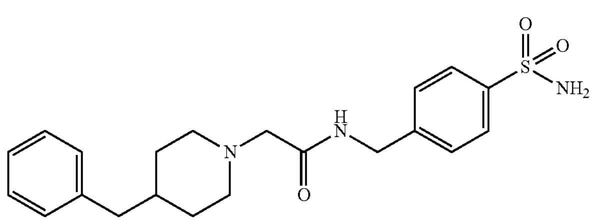 [SMILES: NS(=O)(=O)c1ccc(CNC(=O)CN2CCC(Cc3ccccc3)CC2)cc1] | 39.44 ± 0.76 | III |
| C15 | 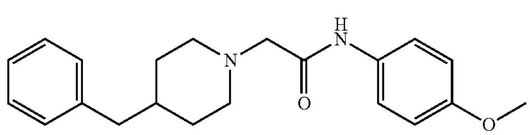 [SMILES: COc1ccc(NC(=O)CN2CCC(Cc3ccccc3)CC2)cc1] | 184.48 ± 3.60 | III |
| C16 | 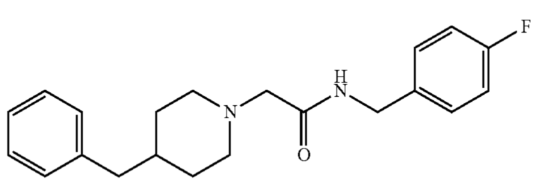 [SMILES: O=C(CN1CCC(Cc2ccccc2)CC1)NCc1ccc(F)cc1] | 484.16 ± 9.44 | III |

TABLE 1-continued

| Comd. NO. | Chemical Structure | IC$_{50}$ (nM) | Formulae |
|---|---|---|---|
| C17 | 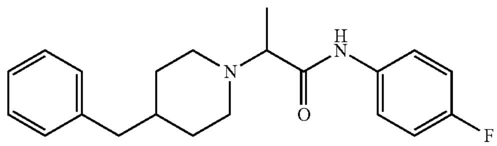 [SMILES: CC(C(=O)Nc1ccc(F)cc1)N1CCC(Cc2ccccc2)CC1] | 278.56 ± 5.43 | IV |
| C18 | 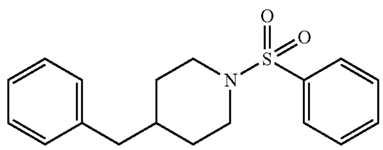 [SMILES: O=S(=O)(c1ccccc1)N1CCC(Cc2ccccc2)CC1] | 112.48 ± 2.19 | I |
| C19 | 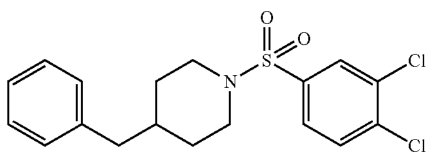 [SMILES: O=S(=O)(c1ccc(Cl)c(Cl)c1)N1CCC(Cc2ccccc2)CC1] | 102.13 ± 1.99 | I |
| C20 | 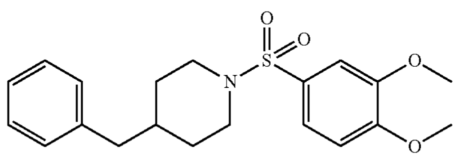 [SMILES: COc1ccc(S(=O)(=O)N2CCC(Cc3ccccc3)CC2)cc1OC] | 63.32 ± 1.23 | I |
| C21 | 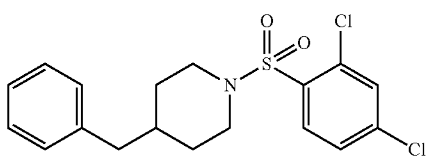 [SMILES: O=S(=O)(c1ccc(Cl)cc1Cl)N1CCC(Cc2ccccc2)CC1] | 41.23 ± 0.80 | I |
| C22 | 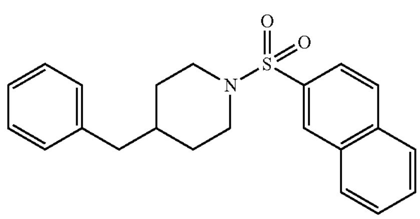 [SMILES: O=S(=O)(c1ccc2ccccc2c1)N1CCC(Cc2ccccc2)CC1] | 244.78 ± 4.77 | I |
| C23 | 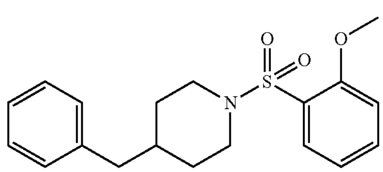 [SMILES: COc1ccccc1S(=O)(=O)N1CCC(Cc2ccccc2)CC1] | 206.75 ± 4.03 | I |
| C24 | 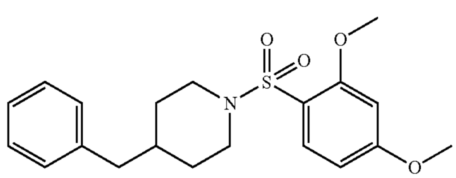 [SMILES: COc1ccc(S(=O)(=O)N2CCC(Cc3ccccc3)CC2)c(OC)c1] | 56.39 ± 1.10 | I |
| C25 | 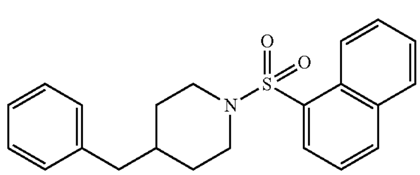 [SMILES: O=S(=O)(c1cccc2ccccc12)N1CCC(Cc2ccccc2)CC1] | 216.09 ± 4.21 | I |

TABLE 1-continued

| Comd. NO. | Chemical Structure | IC$_{50}$ (nM) | Formulae |
|---|---|---|---|
| C26 | 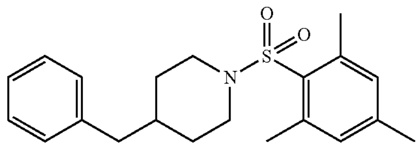 [SMILES: Cc1cc(C)c(S(=O)(=O)N2CCC(Cc3ccccc3)CC2)c(C)c1] | 107.36 ± 2.09 | I |
| C27 | 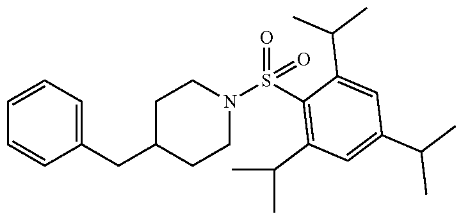 [SMILES: CC(C)c1cc(C(C)C)c(S(=O)(=O)N2CCC(Cc3ccccc3)CC2)c(C(C)C)c1] | 142.87 ± 2.78 | I |
| C28 | 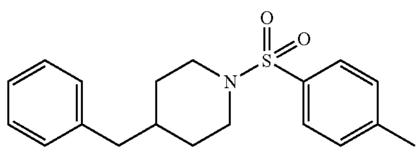 [SMILES: Cc1ccc(S(=O)(=O)N2CCC(Cc3ccccc3)CC2)cc1] | 56.5 ± 1.10 | I |
| C29 | 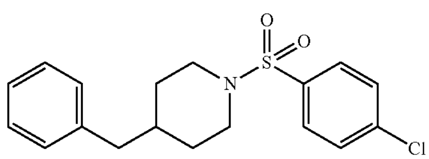 [SMILES: O=S(=O)(c1ccc(Cl)cc1)N1CCC(Cc2ccccc2)CC1] | 250.17 ± 4.88 | I |
| C30 | 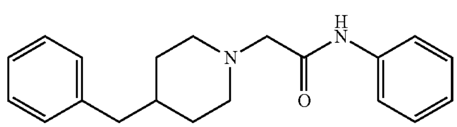 [SMILES: O=C(CN1CCC(Cc2ccccc2)CC1)Nc1ccccc1] | 59.03 ± 1.15 | III |
| C31 | 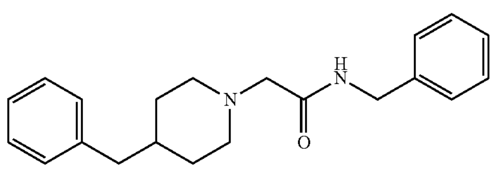 [SMILES: O=C(CN1CCC(Cc2ccccc2)CC1)NCc1ccccc1] | 74.92 ± 1.46 | III |
| C32 | 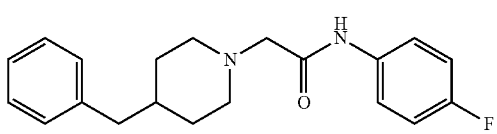 [SMILES: O=C(CN1CCC(Cc2ccccc2)CC1)Nc1ccc(F)cc1] | 202.78 ± 3.95 | III |
| C33 | 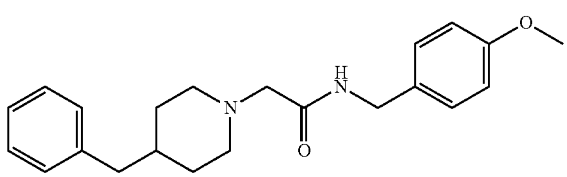 [SMILES: COc1ccc(CNC(=O)CN2CCC(Cc3ccccc3)CC2)cc1] | 99.8 ± 1.94 | III |
| C34 | 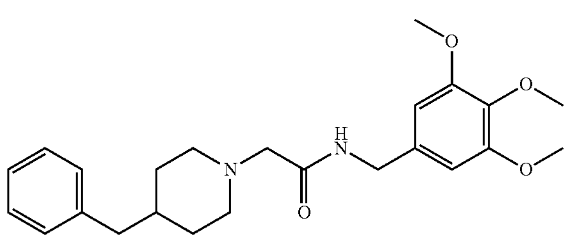 [SMILES: COc1cc(CNC(=O)CN2CCC(Cc3ccccc3)CC2)cc(OC)c1OC] | 60.53 ± 1.18 | III |

TABLE 1-continued

| Comd. NO. | Chemical Structure | IC$_{50}$ (nM) | Formulae |
|---|---|---|---|
| sildenafil | 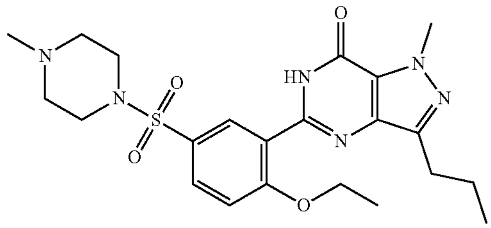 [SMILES: CCCc1nn(C)c2c(=O)[nH]c(-c3cc(S(=O)(=O)N4CCN(C)CC4)ccc3OCC)nc12] | 39.421 ± 0.76 | — |

Phosphodiesterase type 5 (PDE5) inhibition activities.

Example 18

In Vivo Erectile Dysfunction (Tables 2-4 and FIGS. 1-5)

Sexually mature Wistar albino male and female rats weighing 150-180 g (10-14 weeks old) were used in our study. Males were trained for sexual behavior with estrus females, that is, two hours a day for one week, before the investigations. Females were brought into the estrous phase artificially by sequential injection of estradiol benzoate (Sigma) (25 μg/animal) and progesterone (Sigma) (250 μg/animal) subcutaneously, 48 and 4 hours before pairing, respectively. Only those sexually active animals were used subsequently in the study. Sexually active rats were isolated and housed in separate cages at room temperature (24±2° C.) on a reversed day/night cycle with a relative humidity of 50-55% during the experimental period. All sexual studies were performed in a calm laboratory condition under subdued light. For the toxicity study, adult Wistar albino male rats were used separately. Rats were obtained from the Experimental Animal Care Center, College of Pharmacy, King Saud University. Animals were fed with a standard pellet diet and provided water ad libitum. All experiments were performed per the protocols and recommendations of the NIH Guide for the Care and Use of Laboratory Animals and the legal requirements of King Saud University for investigations on humans and animals.

Copulatory Behavior Testing

Based on a preliminary study to select the appropriate dose for the promising synthesized compounds, the compounds were administered separately to sexually experienced male rats by oral gavage at 5 mg/kg in a 0.5% sodium carboxymethyl cellulose (CMC) vehicle. The negative control group administered 0.5% CMC only, whereas the positive control group orally received 5 mg/kg sildenafil. All solutions were freshly prepared at a concentration that allowed the administration of 1 ml/kg.

After drug treatment, rats were housed separately in transparent cages for acclimation. Thirty minutes after drug treatment, a sexually receptive female rat with estrous phase was introduced in each cage for 30 min and the following parameters of the copulatory behavior were recorded: namely mount latency (ML; time from introduction of the female until the first mount with or without penile insertion, it measures the degree of arousal or sexual interest or libido of the male), mount frequency (MF; the number of mounts until ejaculation, it is a measure of the degree of the male's sexual interest or libido), intromission latency (IL; time from introduction of the female until the first intromission, it measures the degree of sexual excitement and erection), intromission frequency (IF; number of vaginal penetrations until ejaculation, it measures the degree of erection), ejaculation latency (EL; time from the first intromission until ejaculation, it determines the excellent organization of copulation in rats) and post-ejaculatory interval (PEI; time interval between an ejaculation and the following first mount, it measures the refractory period that comes after ejaculation). Latency values represent the number of seconds that elapses from the introduction of the female into the copulatory arena until the male executes the first mount, intromission or ejaculation. Frequency values represent the number of ejaculations, mounts or intromission recorded during the copulatory test.

Depending on these parameters, the following can be calculated: Copulatory efficiency (CE)=(IF/MF)×100 and mean intromission interval (MII)=EL/IF as previously described (Aydogan F. et al., J Ethnopharmacol 257 (2020) 112868; Besong E B. et al., Biochem Res Int 2018 (2018) 2869727, the contents of each of which are hereby incorporated by reference in their entirety). Experiments were repeated blindly three times using new fresh (unused) animals in each experiment.

The results displayed in Table 2 demonstrate that sildenafil and compounds C9, C11, C14, C21, C24 and C28 significantly decreased the ML and IL of males as compared to the untreated control group. They also considerably elevated the IF, MF and prolonged EL compared to the untreated controls. These were, however, not significantly different in male animals that were administered compounds C20 and C30. Weak but significant reductions in the IL in animals treated with compound C30 and prolonged EL of male rats treated with compound C20 were only observed. Sildenafil and compounds C9, C14, C21 and C24 statistically decreased the duration of the refractory period between the first and second series of mating (post-ejaculatory interval) was also observed; confirmed that these compounds improved the sexual activity of treated rats. The proportion of CE was the highest in the rats treated with sildenafil, compounds C9, C11, C14, C21, C24 and C28 compared to the untreated control group (Table 2, FIG. 1A). A statistical decrease in the MII of male rats was detected in sildenafil and compounds C9, C11, C14, C21, C24 and C28 treated groups compared to the untreated control rats (Table 2, FIG. 1B). On the contrary, administrations of compounds C20 and C30 did not alter the CE and MII when compared to the control animals. Overall, the efficacy of the synthesized compounds in improving copulatory behavior was more pronounced after treatment with compounds C9, C11, C14, C21, C24 and C28, while sildenafil and compounds C9, C14 and C21 exhibited their highest effects after treatment.

TABLE 2

| Groups | MF | ML (sec) | IF | IL (sec) | EL (sec) | PEI (sec) | CE (%) | MII |
|---|---|---|---|---|---|---|---|---|
| Control | 13.8 ± 2.4 | 109.8 ± 12.8 | 5.3 ± 1.2 | 256.3 ± 28.7 | 288.3 ± 19.5 | 445.1 ± 45.0 | 38.6 ± 5.9 | 56.7 ± 14.9 |
| Sildenafil | 26.6 ± 4.5** | 68.5 ± 10.6** | 17.8 ± 2.4** | 135.1 ± 6.9** | 426.6 ± 27.6** | 294.5 ± 28.6** | 67.2 ± 4.1** | 24.3 ± 4.3** |
| C 9 | 23.6 ± 3.3** | 74.6 ± 9.8** | 12.8 ± 1.9** | 177.6 ± 13.9** | 368.3 ± 21.1** | 355.6 ± 43.0** | 55.2 ± 11.6* | 29.0 ± 3.1** |
| C 11 | 17.1 ± 1.7* | 94.6 ± 6.4* | 8.3 ± 1.7** | 205.5 ± 26.2** | 318.1 ± 35.9 | 393.5 ± 37.7 | 48.5 ± 8.7* | 39.6 ± 9.6* |
| C 14 | 27.3 ± 5.1** | 54.6 ± 6.3** | 20.6 ± 2.7** | 122.6 ± 8.6** | 425.1 ± 17.2** | 277.1 ± 28.6** | 76.2 ± 5.4** | 20.8 ± 2.8** |
| C 30 | 14.8 ± 1.7 | 95.5 ± 10.2 | 6.8 ± 1.4 | 215.3 ± 14.3* | 324.6 ± 39.0 | 411.8 ± 21.3 | 46.8 ± 12.4 | 49.2 ± 11.2 |
| C 20 | 16.0 ± 3.1 | 95.5 ± 12.4 | 7.6 ± 1.6 | 229.1 ± 42.6 | 325.1 ± 25.1* | 401.8 ± 39.3 | 48.5 ± 9.3 | 44.7 ± 13.5 |
| C 21 | 26.6 ± 2.7** | 72.5 ± 8.3* | 16.8 ± 1.8** | 178.6 ± 12.9** | 395.0 ± 28.0** | 298.0 ± 37.2** | 63.6 ± 9.3** | 23.74 ± 3.5** |
| C 24 | 17.3 ± 2.5* | 85.0 ± 8.4** | 9.3 ± 1.6** | 193.8 ± 21.4** | 377.6 ± 33.0** | 370.0 ± 36.2** | 54.0 ± 8.4** | 41.2 ± 6.4* |
| C 28 | 17.5 ± 1.6* | 94.6 ± 10.3* | 9.1 ± 1.1** | 195.5 ± 20.3** | 332.8 ± 19.1** | 393.3 ± 37.2 | 52.3 ± 4.1** | 36.6 ± 3.8** |

Table 2. Influence of sildenafil and synthesized compounds at 5 mg/kg on the mount frequency (MF), mount latency (ML), intromission frequency (IF), intromission latency (IL), ejaculation latency (EL), post-ejaculatory interval (PEI), copulatory efficiency (CE) and mean intromission interval (MII) of male rats.

Copulatory Behavior Testing in Diabetic Animals.

Nearly 90% of the population suffering from diabetic conditions report disturbances in sexual function, encompassing a decrease in libido, impotence and infertility (Kamenov Z A, Exp Clin Endocrinol Diabetes 123 (2015) 141-158). Diabetic was induced in experimental animals by intraperitoneal administration of streptozotocin in separate groups of male animals. Diabetes was induced by a single intraperitoneal injection of freshly prepared 65 mg/kg streptozotocin in 0.1 mM citrate buffer, pH 4.4 (Mendez J D and Ramos H G, Arch Med Res 25 (1994) 367-375). All rats receiving streptozotocin were given a 10% sucrose solution in the first 48 h after injection to prevent hypoglycemia. After 72 h of streptozotocin administration, rats with fasting serum glucose more than 350 mg/dL were considered as diabetic. Glibenclamide was given by oral gavage once a day (10 mg/kg/day) to diabetic animals to avoid mortality throughout the investigation (Abdel-Aziz A A-M. et al., Eur J Med Chem 46 (2011) 4324-4329). The male rats were trained for sexual behavior study before induction of diabetes and treatment, as mentioned above. Diabetic rats were given a daily oral dose of 5 mg/kg of compounds C9, C14 and C21 for 14 consecutive days. The sexual behavior of the animals was assessed on day 15 of the treatment. The copulatory behavior testing was performed, and CE and MII were calculated.

Streptozotocin induced hyperglycemic rats showed an overall reduced sexual performance. The hyperglycemia in sexually active male rats significantly decreased MF, IF, and EL and increased ML, IL and PEI compared to non-diabetic normal rats. Treatment with compounds C9, C14 and C21 restored the sexual function in diabetic rats, as evidenced by an increase in MF, IF, and EL and a decrease in ML, IL and PEI compared to diabetic control rats. Consequently, the percentages of CE were increased, and MII were decreased to levels that significantly differed from diabetic animals (Table 3, FIGS. 2A and 2B).

TABLE 3

| Groups | MF | ML (sec) | IF | IL (sec) | EL (sec) | PEI (sec) | CE (%) | MII |
|---|---|---|---|---|---|---|---|---|
| Control | 12.6 ± 2.5 | 110.5 ± 16.4 | 4.8 ± 1.9 | 251.6 ± 19.7 | 298.1 ± 16.3 | 464.6 ± 40.3 | 36.9 ± 7.6 | 69.9 ± 25.7 |
| Diabetic | 4.8 ± 0.9** | 215.5 ± 34.2** | 1.16 ± 0.4** | 520.6 ± 55.7** | 139.0 ± 41.0** | 794.0 ± 80.4** | 24.1 ± 5.6** | 121.0 ± 18.4** |
| C9 (Adalafil-1) | 10.6 ± 2.5$^b$ | 137.1 ± 17.4$^b$ | 4.3 ± 1.2$^b$ | 305.1 ± 59.2$^b$ | 223.3 ± 63.7$^a$ | 552.8 ± 49.6$^a$ | 40.9 ± 7.8$^b$ | 53.1 ± 16.3$^a$ |
| C 14 (Adalafil-2) | 10.6 ± 1.2$^b$ | 158.0 ± 13.2$^b$ | 3.8 ± 0.9$^b$ | 327.6 ± 45.9$^b$ | 208.3 ± 32.5$^b$ | 505.6 ± 62.4$^b$ | 35.6 ± 6.4$^a$ | 55.7 ± 7.8$^b$ |
| C 21 (Adalafil-3) | 10.6 ± 1.6$^b$ | 154.6 ± 6.3$^b$ | 4.3 ± 0.8$^b$ | 326.0 ± 19.5$^b$ | 248.5 ± 26.2$^b$ | 510.5 ± 50.1$^b$ | 41.1 ± 8.9$^b$ | 59.1 ± 13.0$^b$ |

Influence of sildenafil and synthesized compounds 9, 14 and 21 (5 mg/kg/day for 14 days) on the mount frequency (MF), mount latency (ML), intromission frequency (IF), intromission latency (IL), ejaculation latency (EL), post-ejaculatory interval (PEI), copulatory efficiency (CE) and mean intromission interval (MII) of male diabetic rats.

Each value represents the mean of three independent experiments ± SD. *P < 0.05 and **P < 0.01 versus control and $^a$P < 0.05 and $^b$p < 0.01 versus diabetic rats (Student's t-test).

Penile Erection Index (PEI)

The penile erection index is an established means of determining the erection promoting properties of a substance. Determination of penile erection in a noncontact position was calculated as reported previously (Haripriya V M. et al., Andrologia 51 (2019) e13180; Sharma V. et al., J Ethnopharmacol 143 (2012) 201-206, the contents of each of which are hereby incorporated by reference in their entirety). The sexually experienced male rats of all groups were given the treatment 30 minutes before experimentation. The number of animals for each dose was ten rats in each experiment. The doses of sildenafil and selected compounds C9, C14, and C21 were 1.25, 2.5 and 5 mg/kg. The results shown are the average of three separate experiments. Control animals were given 0.5% CMC as a vehicle.

The rats of each group were placed in the observation cages (five at a time) divided into half by two sheets of metal mesh, preventing contact but allowing auditory, visual and olfactory stimuli. After a 5-min adaptation period, the test was started by placing an estrus female on the other side of the cage. Penile erection was recorded when the rats bent down to lick their erect penis. Homosexual mounting was also counted when a male rat mounted another male rat performing pelvic thrusts with or without a penile erection. The degree of sexual stimulation in each group was expressed as the penile erection index, achieved by multiplying the mean of penile erections per animal by the percentage of rats exhibiting at least one episode of penile erection throughout the 30 min surveillance period. The effective dose $ED_{50}$ (the dose required to give 50% responding rats) for examined compounds was calculated using linear regression analysis by GraphPad software with the proportion of responding rats as the input data and expressed as µmol/kg.

Figure 3:
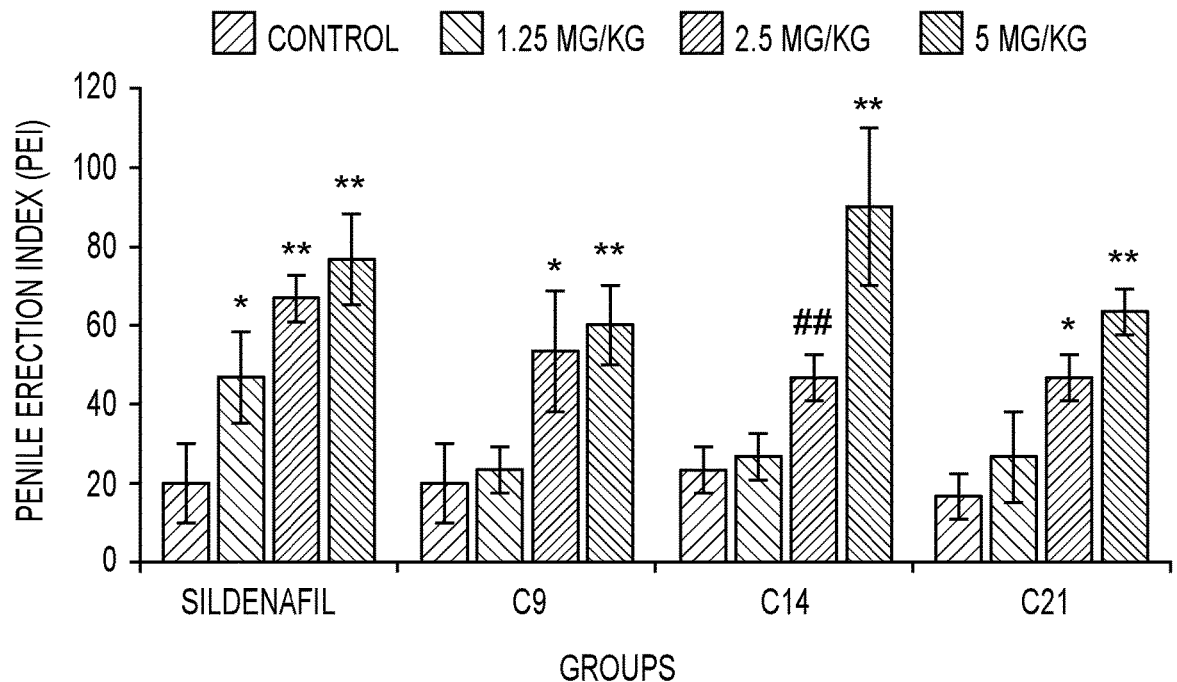
FIG. 3 shows the effect of oral administration of sildenafil and compounds C9, C14, and C21 on enhancing sexual activity in rats. The figure shows the penile erection index (PEI) in relation to an increased dose. Each value represents the mean of three independent experiments±SD. *P<0.05 and **P<0.01 versus control (ANOVA-test). ##P<0.01 versus control (Student's t-test).
Figure 4:
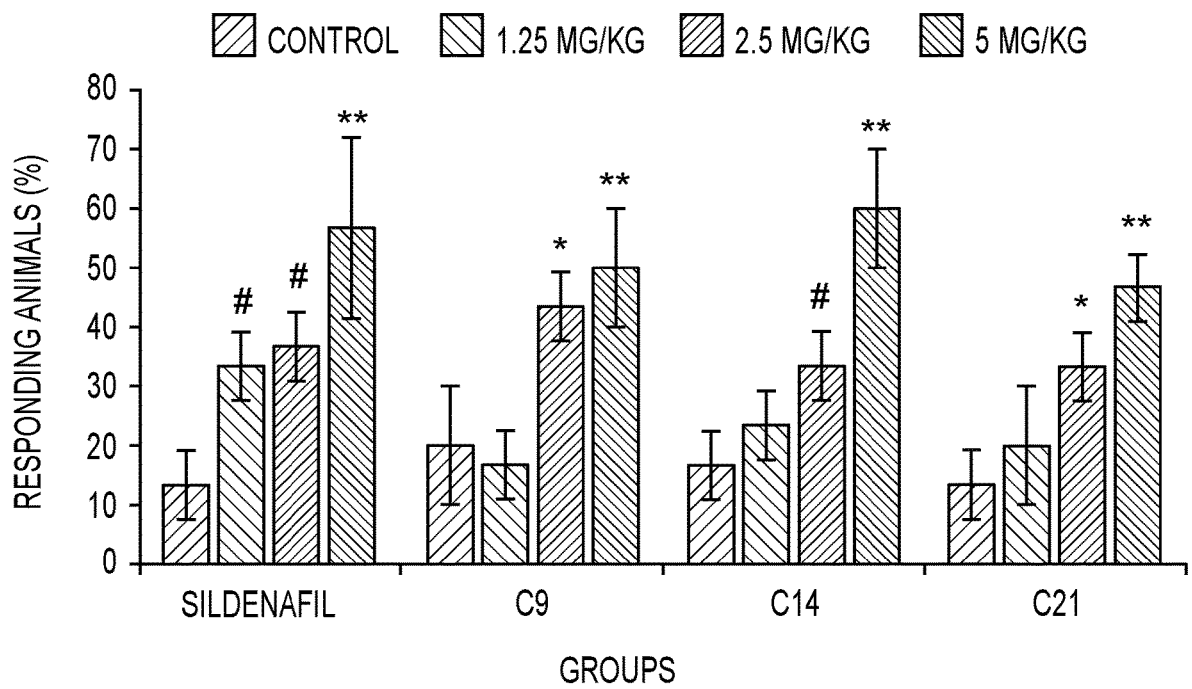
FIG. 4 shows the effect of oral administration of sildenafil and compounds C9, C14, and C21 on enhancing sexual activity in rats. The figure shows the percentage of active animals in relation to increased dose. Each value represents the mean of three independent experiments±SD. *P<0.05 and **P<0.01 versus control (ANOVA-test). #P<0.05 versus control (Student's t-test).
Figure 5:
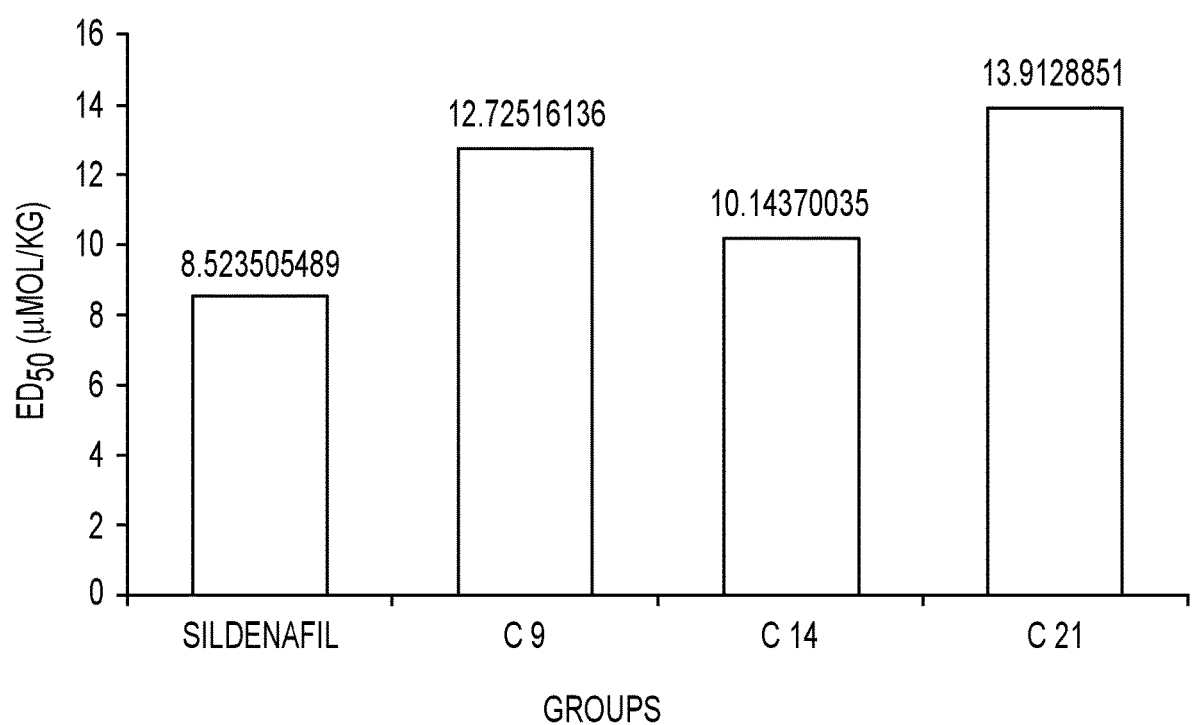
FIG. 5 shows the effective dose, as represented by $ED_{50}$ for sildenafil and compounds C9, C14, and C21. The effective dose was the concentration required to initiate sexual activity in 50% of the experimental animals under study. This was calculated from the number of active animals at each concentration and presented as μmol/kg.

As presented in Table 4 and FIGS. 3-5, the erectile response was statistically elevated upon the oral treatment of compounds C9, C14, and C21, which presented a similar trend as the positive control sildenafil. In all groups, the penile erection index significantly improved with increasing doses but without significant homosexual mountings during the observation period. As presented in Table 4 and FIGS. 3-5, the percentage of responding animals to this treatment increased markedly in all treated groups. In Table 4, *P<0.05 and **P<0.01 versus control (ANOVA-test). ##P<0.01 versus control.

FIG. 3 shows the penile erection index (PEI) in relation to an increased dose. FIG. 4 shows the percentage of active animals in relation to increased dose. Each value represents the mean of three independent experiments±SD. *P<0.05 and **P<0.01 versus control (ANOVA-test). #P<0.05 versus control. Each value represents the mean of three independent experiments±SD. FIG. 5 shows Comparison of effective dose for sildenafil and compounds 9, 14 and 21. The effective dose was the concentration required to initiate sexual activity in 50% of the experimental animals under study. This was calculated from the number of active animals at each concentration and presented as µmol/kg. The maximum increase in the proportion of responding rats was achieved at 5 mg/kg for all compounds.

It is clear from the increasing animal response and line regression analysis that a dose-dependent positive response was obtained for all drugs, with compound 14 giving a higher response. However, the effective dose $ED_{50}$ was calculated as 10.14 and 8.52 µmol/kg body weight for compound 14 and sildenafil, respectively. Moreover, $ED_{50}$ for compounds 11 and 21 was 12.72 and 14.32, respectively.

TABLE 4

Effect of oral administration of compounds C9, C14, C21, and sildenafil on enhancing sexual activity in rats

| Treatment | Compound 9 | Compound 14 | Compound 21 | Sildenafil |
|---|---|---|---|---|
| Control | 20.0 ± 5.7 | 23.3 ± 3.3 | 16.6 ± 3.0 | 20.0 ± 5.8 |
| Dose 1.25 mg/kg | 23.3 ± 3.3 | 26.6 ± 3.4 | 26.5 ± 6.6 | 46.6 ± 3.4* |
| Dose 2.5 mg/kg | 53.3 ± 8.8* | 46.6 ± 3.3* | 46.6 ± 3.3* | 66.5 ± 3.0** |
| Dose 5 mg/kg | 60.0 ± 5.7** | 90.0 ± 11.5** | 63.3 ± 3.4** | 76.6 ± 6.7** |

The table shows the penile erection index (PEI) in relation to increased dose. Each value represents the mean of three independent experiments ± SD. *P < 0.05 and **P < 0.01 versus the corresponding control group (ANOVA-test followed by Tukey-Kramer test for multiple comparisons).

Evaluation of $LD_{50}$ of Most Active Compounds

Healthy rats were divided into groups of 10 rats and maintained as described above. Rats had free access to water and food, except for a short fasting period before the treatment with the single oral dose of compounds C9, C14 and C21 or the solvent. The compounds were formulated with 1% CMC. An approximate $LD_{50}$ was initially determined in a pilot study by a so called 'staircase method' using a small number of animals (2 each dose) and increasing doses of tested compounds. Three doses were then chosen for the determination of oral median lethal dose (LDso) (500, 1000 and 2000 mg/kg) and given to three groups of rats (10 in each group). Another group of rats (6 rats) was given equal amounts of 1% CMC orally and served as a control group. The animals were observed for the first two hours and then at $6^{th}$ and $24^{th}$ hours for any toxic symptoms. After 24 hours, the number of dead rats was counted in each group. The percentage of animals that had died at each dose level was transformed to probits, and then $LD_{50}$ was determined by the method of Miller and Tainter, 1944 as described previously (Randhawa M A, J Ayub Med Coll Abbottabad 21 (2009) 184-185, the contents of which are hereby incorporated by reference in their entirety).

The $LD_{50}$ in rats for the compounds with broad activities (compounds C9, C14 and C21) was evaluated by single intragastric administration. The $LD_{50}$ of compounds C9, C14 and C21 was determined to be >2000 mg/kg. The animals receiving oral compounds C9, C14 and C21 gradually became drowsy and less responsive. The severity of these effects was related to the level of dose. However, at six hours, most survivors recovered from these symptoms. No mortality or symptoms were similar to those obtained after the treatment of the tested compound observed in the vehicle-treated control animals. These results indicate that the three compounds exhibit low toxicity and are well tolerated by experimental animals.

It is to be understood that the 1,4-disubstituted piperidine compounds are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A compound selected from the group consisting of:
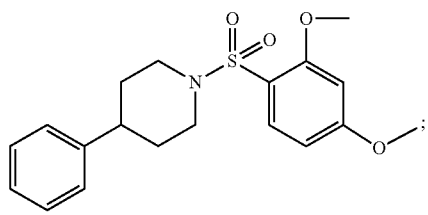 (C1)
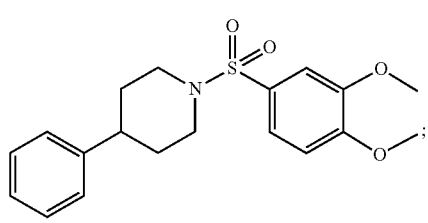 (C2)
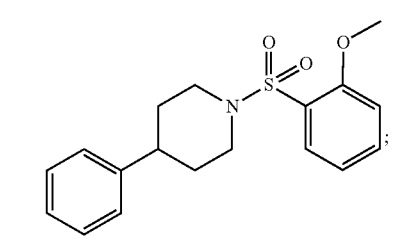 (C3)
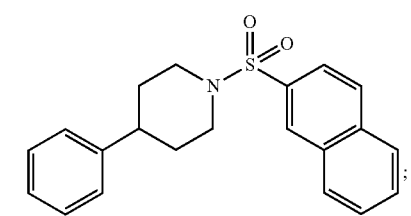 (C4)
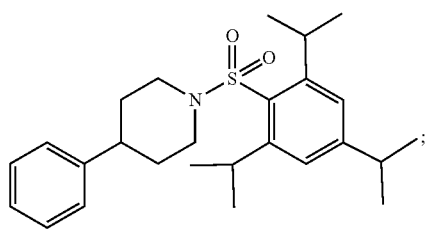 (C7)
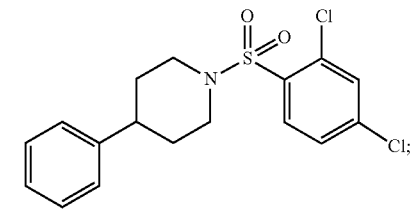 (C9)
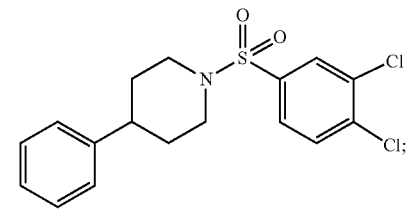 (C11)
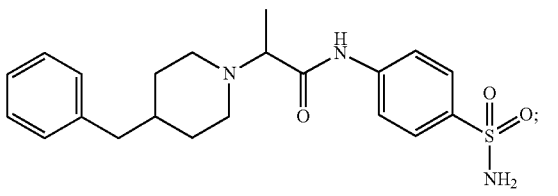 (C12)
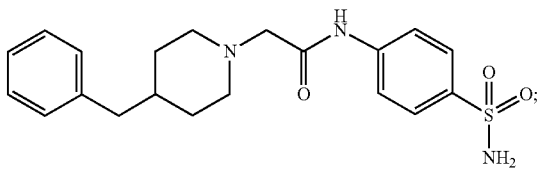 (C13)
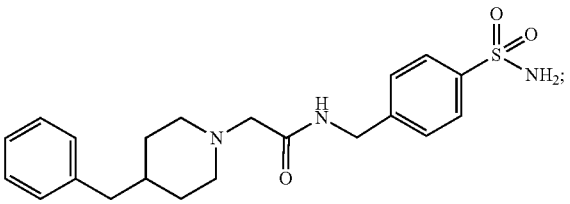 (C14)
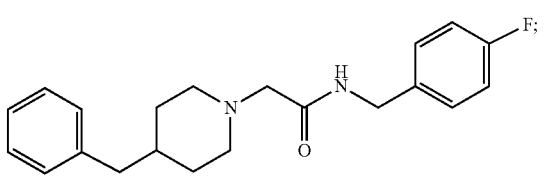 (C16)
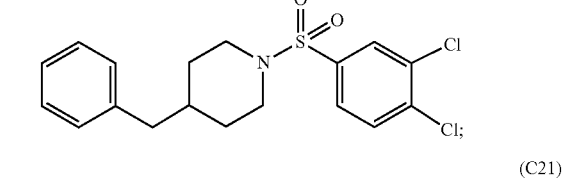 (C19)
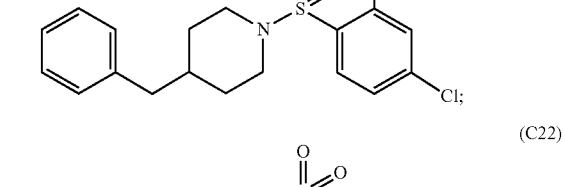 (C21)
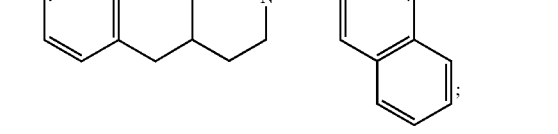 (C22)
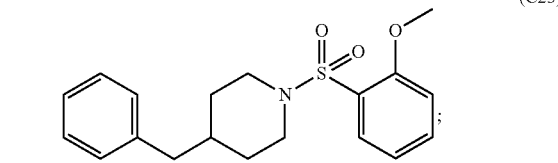 (C23)

(C25) 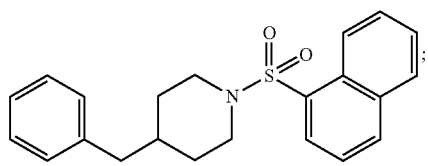

(C26) 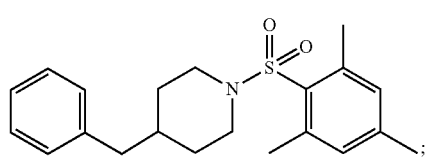

(C27) 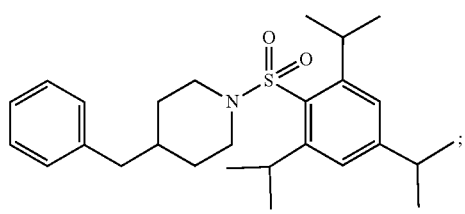

(C33) 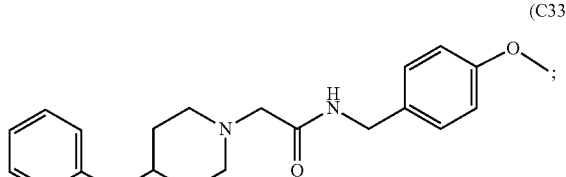

(C34) 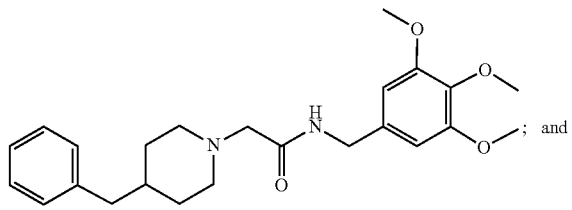 and a pharmaceutically acceptable salt, ester, stereoisomer, or solvate thereof.

2. A pharmaceutically acceptable composition comprising a therapeutically effective amount of the compound of claim 1 and a pharmaceutically acceptable carrier.

3. A method of treating erectile dysfunction in a patient, comprising administering to a patient in need thereof a therapeutically effective amount of the compound of claim 1.

* * * * *